US010285625B2

United States Patent
Hawkins, III et al.

(10) Patent No.: US 10,285,625 B2
(45) Date of Patent: May 14, 2019

(54) ACTIVITY MONITORING COMPUTING DEVICE AND SYSTEM

(71) Applicant: Wahoo Fitness LLC, Atlanta, GA (US)

(72) Inventors: Harold M. Hawkins, III, Atlanta, GA (US); Michael A. Lyle, Gainesville, GA (US); Bradley Jaymes Collins, Atlanta, GA (US); Christopher Luke Uroda, Oxley (AU); Mark Snaterse, Oegstgeest (NL)

(73) Assignee: Wahoo Fitness LLC, Atlanta, GA (US)

( * ) Notice: Subject to any disclaimer, the term of this patent is extended or adjusted under 35 U.S.C. 154(b) by 1070 days.

(21) Appl. No.: 14/508,799

(22) Filed: Oct. 7, 2014

(65) Prior Publication Data

US 2015/0099945 A1    Apr. 9, 2015

Related U.S. Application Data

(60) Provisional application No. 61/887,730, filed on Oct. 7, 2013, provisional application No. 61/979,382, filed on Apr. 14, 2014, provisional application No. 62/046,763, filed on Sep. 5, 2014.

(51) Int. Cl.
| | |
|---|---|
| *A61B 5/11* | (2006.01) |
| *A61B 5/00* | (2006.01) |
| *A61B 5/0245* | (2006.01) |
| *A61B 5/024* | (2006.01) |
| *G01C 22/00* | (2006.01) |

(52) U.S. Cl.
CPC .......... *A61B 5/1118* (2013.01); *A61B 5/0245* (2013.01); *A61B 5/02438* (2013.01); *A61B 5/6823* (2013.01); *A61B 5/6831* (2013.01); *A61B 5/7235* (2013.01); *G01C 22/002* (2013.01); *G01C 22/006* (2013.01)

(58) Field of Classification Search
CPC .......................... A61B 5/1118; A61B 5/02438
See application file for complete search history.

(56) References Cited

U.S. PATENT DOCUMENTS

| | | | | |
|---|---|---|---|---|
| 7,753,861 | B1 * | 7/2010 | Kahn | A61B 5/1118 482/8 |
| 8,011,242 | B2 * | 9/2011 | O'Neill | G01L 3/242 73/379.01 |
| 8,436,737 | B1 * | 5/2013 | Trout | A61B 5/1116 340/573.1 |
| 9,075,076 | B2 * | 7/2015 | Baechler | B62J 99/00 |
| 9,877,667 | B2 * | 1/2018 | Doheny | A61B 5/1116 |

(Continued)

*Primary Examiner* — John R Downey
(74) *Attorney, Agent, or Firm* — Polsinelli PC

(57) ABSTRACT

An activity monitoring device (AMD) wearable on the torso of a user. The AMD including functional components such as an accelerometer, a processor, on-board data memory, a wireless transmitter and electrodes for detecting heart rate. The functional components configured to collect data in order to provide heart rate information, running speed, ground contact time, vertical oscillation, cycling cadence, riding positions (standing or seated) and other functions. The device may be accessed and controlled by way of the wireless connection. The device and/or functions thereof may also be controlled through accurate user tap detection. The device may further store and transmit information relevant to various functions for remote storage or display.

19 Claims, 16 Drawing Sheets

(56) References Cited

U.S. PATENT DOCUMENTS

| | | | |
|---|---|---|---|
| 2002/0082491 A1* | 6/2002 | Nissila | A61B 5/024 600/391 |
| 2005/0283205 A1* | 12/2005 | Lee | A61B 5/0488 607/48 |
| 2010/0024590 A1* | 2/2010 | O'Neill | G01L 3/242 74/594.1 |
| 2012/0246795 A1* | 10/2012 | Scheffler | A41D 1/002 2/69 |
| 2013/0205896 A1* | 8/2013 | Baechler | B62J 99/00 73/493 |

* cited by examiner

ACTIVITY MONITORING COMPUTING DEVICE AND SYSTEM

CROSS-REFERENCE TO RELATED APPLICATIONS

This application claims priority under 35 U.S.C. § 119 from U.S. provisional application No. 61/887,730 entitled "ACTIVITY MONITORING DEVICE AND SYSTEM," filed on Oct. 7, 2013, U.S. provisional application No. 61/979,382 entitled "ACTIVITY MONITORING COMPUTING DEVICE AND SYSTEM," filed on Apr. 14, 2014, and U.S. provisional application No. 62/046,763 entitled "ACTIVITY MONITORING COMPUTING DEVICE AND SYSTEM," filed on Sep. 5, 2014 the entire contents of which are fully incorporated by reference herein for all purposes.

TECHNICAL FIELD

Aspects of the present disclosure involve wearable activity monitoring and recording devices, and more particularly a monitoring device and system that may be used to detect and record heart rate and movements, and compute various activity and fitness metrics, among other functions.

BACKGROUND

There is a large and growing segment of society focused on fitness, athletic performance, and health. Many of these people are attempting to improve their performance in some event or athletic endeavor, or attempting to reach some personal or professional goal. Moreover, they are often seeking ways to measure and monitor their activity and to understand how any activity improves their performance and health. This is true for elite athletes, so-called "weekend warriors" and people simply trying to live a healthier life style.

In running and biking, for example, it is typical for a person to measure the time it takes to travel some distance and to measure their heart rate. For bicyclists, it is also typical to measure their cycling cadence. When the runner or biker can improve their time, lower their heart rate, increase their cadence relative to heart rate, or realize other positive changes, they understand that their training methods are leading to measurable improvements.

It is with these issues in mind, among others, that aspects of the present disclosure were conceived.

SUMMARY

A device comprising a housing coupled with a strap configured to secure the housing to the torso of a user. A computing unit is disposed within the housing and in communication with a pair of electrodes, the pair of electrodes configured to detect heart rate signals from a user, the computing unit coupled with a memory to store processed heart rate signals. The device further includes an accelerometer in communication with the computing unit. The accelerometer configured to communicate acceleration data associated with movements of the user to the processor, the processor further configured to store processed movement data in the memory.

The device is configured to collect data and to provide various movement related calculation directly or through transmission of the data to other devices. For example, the device may further have the accelerometer configured to generate sets of at least a first acceleration value along a first axis, a set of second acceleration values along a second axis, and a set of third acceleration values along a third axis. These axes may be forward/backward, vertical, and side-to-side. The computing unit may be configured to obtain data for processing a running smoothness metric where the metric is a function of a resultant jerk cost calculation using at least one of the first acceleration values, the second acceleration values and the third acceleration values, or combinations thereof.

These and other aspects of the technology described are provided in additional detail below.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. It should be noted that the drawings are not necessarily to scale; however the emphasis instead is being placed on illustrating the principles of the inventive concepts. Also, in the drawings the like reference characters may refer to the same parts or similar throughout the different views. It is intended that the embodiments and figures disclosed herein are to be considered illustrative rather than limiting.

DETAILED DESCRIPTION

Aspects of the present disclosure involve a wearable activity monitoring and recording device. This disclosure encompasses a variety of integrated and uniquely innovative advances in wearable activity monitoring technology. The device is applicable to a host of activities including walking, running, biking, swimming, and numerous other forms of fitness and other activities that involve human movement. The device and the functionality discussed herein may perform some or all of the functions independently or in conjunction with an interconnected mobile computing platform or other form of computing platform. Thus, references to the device and various methodologies discussed herein may include related and/or coordinated functionality of other computing devices.

To interact with the device, a user may access functionality from an app running on a smart phone using an application programming interface (API) function, for example. Alternatively or additionally, a user may initiate, control and otherwise interact with the device through taps. As discussed herein, aspects of the present disclosure involve innovative mechanisms to distinguish actual taps from a user from any myriad of possible false positives. The device detects and determines walking or running cadence, and is able to calculate distance and pace, again distinguishing from events that are not footsteps and hence not applicable to cadence, etc. The device, in some instances, is able to optimize accuracy of such measurements by correlating heart rate and/or calibration techniques. Moreover, the device is able to avoid steps or functionality that introduce noise and result in inaccurate determinations. In yet another aspect the device is also able to accurately determine vertical oscillation (step height) for a runner or walker.

The device may further be configured to detect cycling cadence and cycling posture (e.g., sitting or standing). Conventionally, cycling cadence is detected using a device that directly counts wheel rotation. The present device may calculate cycling cadence using rider torso movements. Since cycling may involve a variety of body movements, the device is able to discriminate between events seemingly related to cadence and actual cadence events to more accurately determine cadence. Because the device also includes heart rate measurements and possibly other measurements, and storage, a user is able to obtain and/or record cycling related activity metrics without separate and distinct bike mounted equipment. Such a function is particularly useful for indoor cycling (IC) (sometimes referenced as "spin") classes where the user is riding an IC bike in a club but does not have their personal cycling computers mounted to the bike and is nonetheless able to record detailed metrics of a ride. The device also, in some implementations, identifies user position, such as standing or seated, on a bike by identifying accelerometer signal characteristics and removing false events.

Figure 1:
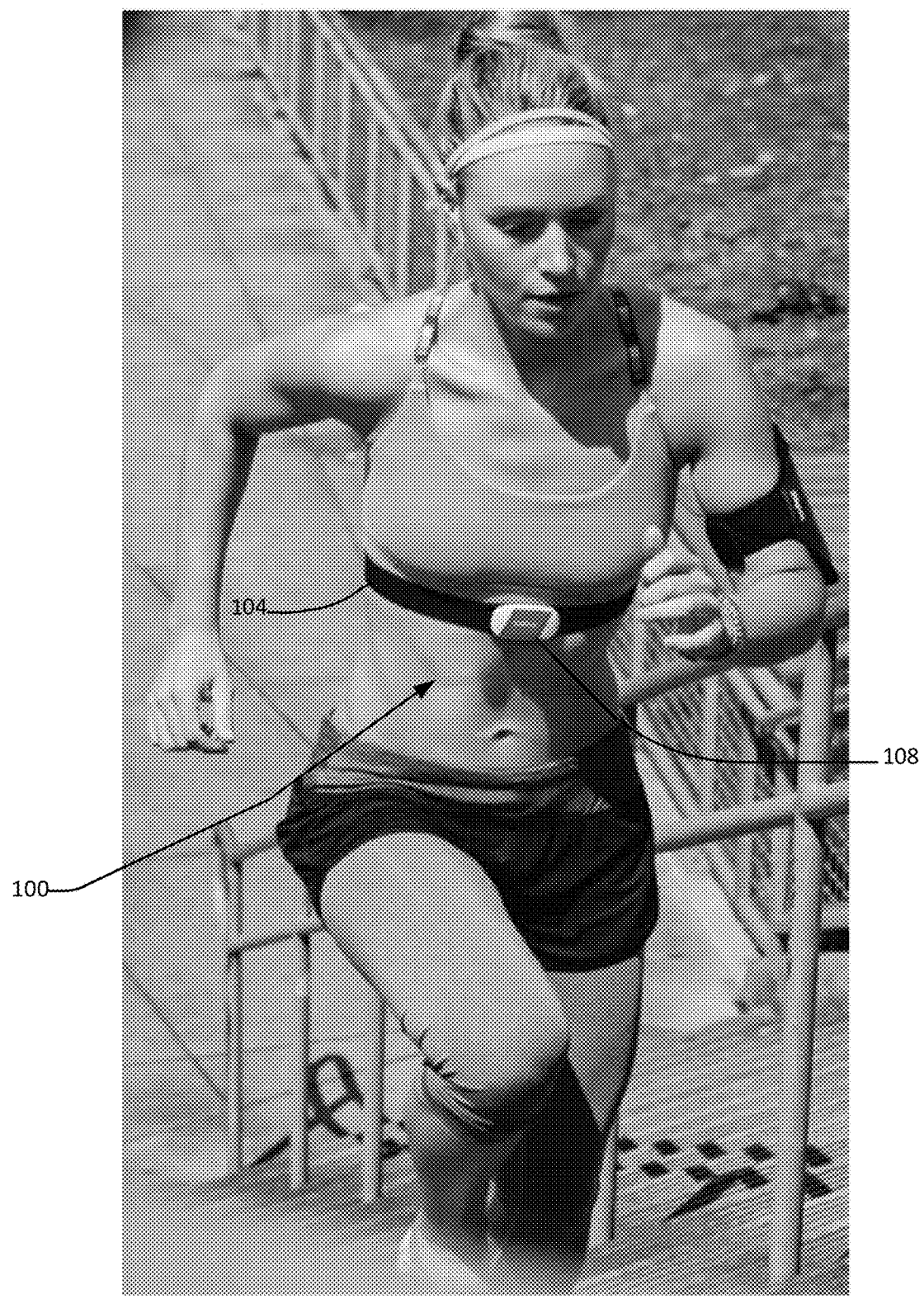
FIG. 1 is a diagram depicting an activity monitoring device strapped to the torso of a user.
Figure 2:
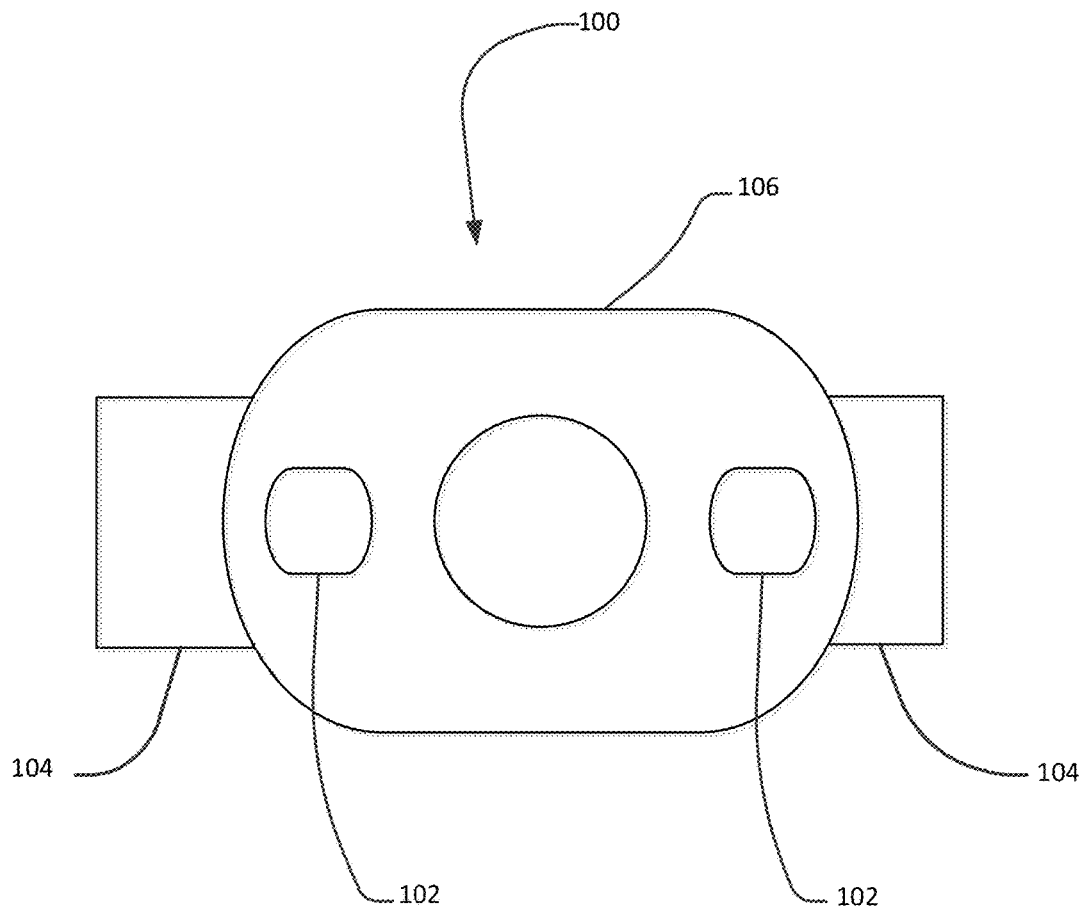
FIG. 2 is a diagram depicting one example of an activity monitoring device having electrodes integrated in a housing of the device.

As illustrated in FIG. 1, the device 100 is configured to be worn on a person's torso, and has two electrodes that detect electrical signals associated with heart contractions. Although not shown in FIG. 1, the electrodes are on the side of a strap 104 that contacts the user's chest. The electrodes are positioned to either side of the housing of the device. However, as shown in FIG. 2, the electrodes may be also be integrated with a housing 106 of the device. Unlike conventional chest worn heart rate monitors that wirelessly transmit heart rate information continuously to a secondary display device such a watch or a bike computer, the present device may store the heart rate data in a local memory, and can be controlled to transmit or not transmit signals to a secondary device, such as a smart phone, smart watch, tablet, dedicated display device, personal computer, or other computing device with a display, for real-time display or storage (see, e.g., FIG. 8). Alternatively, the device may store the heart rate data, in raw or processed form, and transmit the data to a separate device for display, storage, synchronization with cloud storage, synchronization with social activity apps, and the like. Accordingly, the present device is suitable for providing real-time display of various detected and calculated parameters as well as recording those parameters for later display, processing, analyzing, and/or sharing.

Figure 3:
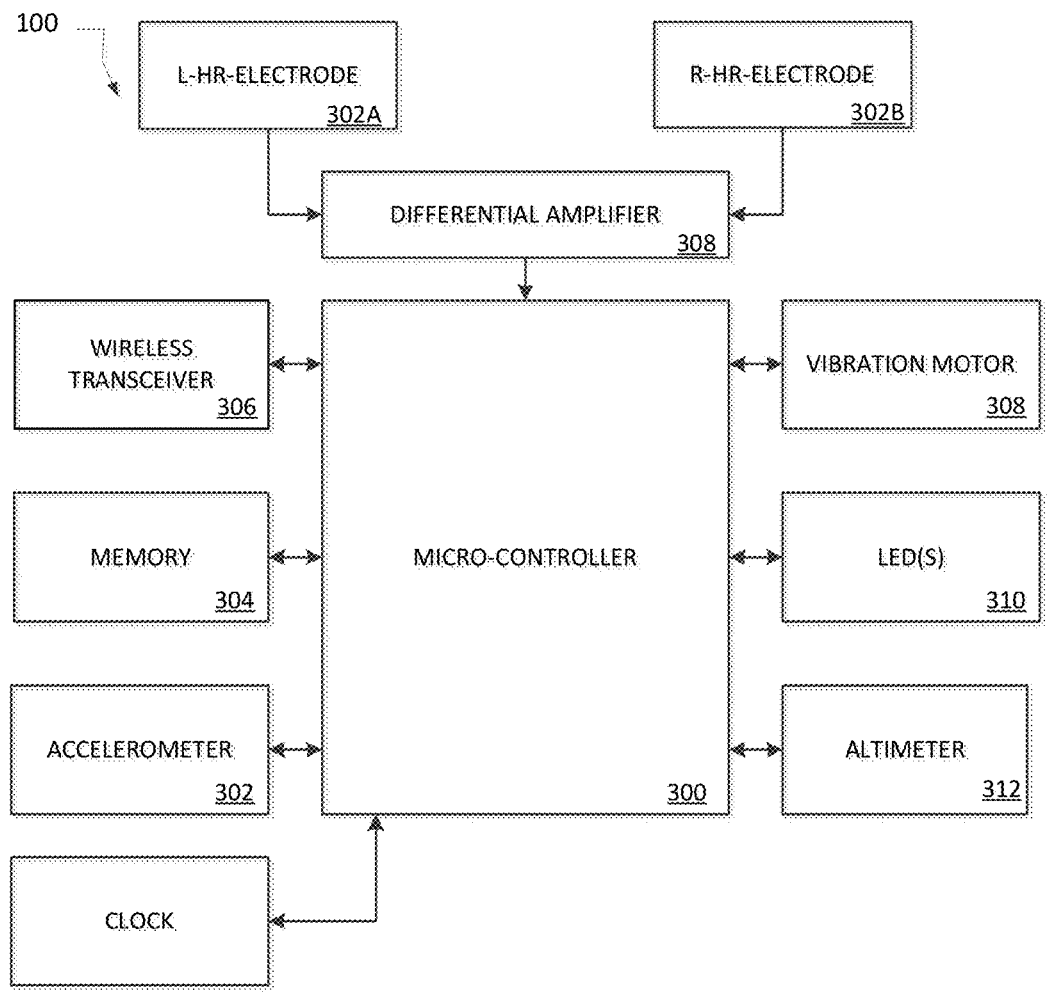
FIG. 3 is an electrical block diagram of one example of a plurality of functional components of the activity monitoring device.

FIG. 3 illustrates one possible electrical architecture for a device conforming to aspects of the disclosure. The device 100 includes a computing unit 100, such as a microcontroller 300, or similar device, such as an ARM Cortex M0 or TI MSP430, in communication with an onboard memory 304. An accelerometer 302, such as a 3-dimensional accelerometer, is coupled with the micro-controller. The device includes the accelerometer and the controller to obtain and record, in the memory 304, the wearer's accelerations (and decelerations) through three dimensional space. The accelerometer information is used to detect walking or running cadence, and from the cadence information calculate distance traveled, in one example. The accelerometer information is also used in many other functionalities discussed herein. Being positioned on the user's chest provides the device with several unique attributes due to the association between the movement of the chest and numerous activities. In this regard, the accelerometer data may be used to detect, filter, and count various forms of movement reflected in the recorded data and experienced or reflected by movement in the wearer's chest.

For example, the device may count and record laps swum in a pool, may count and record push-ups, sit-ups, pull-ups, squats, box-jumps, etc. Through an open application programming interface (API) that provides developers with access and control of the various parameters of the device, countless applications of the device and its data are possible. For example, the device may track and record a user through a diverse fitness routine of running, jumping, sprinting, repetitive strength drills, and other actions detectable and discriminable by the system. The user can then upload the information and compare it to earlier performances from a repeat (count) perspective, a time perspective, a heart rate perspective or other perspectives. The user may also compare performance to other user's through social media fitness apps.

In the specific example of running, with three degrees of acceleration data, the device can also calculate a running efficiency metric taking into account side-to-side wobble, vertical bobbing, and deceleration or "braking" among other movements accompanying many runner's forms. Further, as discussed below, the device may also calculate a running smoothness metric and vertical oscillation metric, among others, and then record those values or generate audible tones, illuminate an LED device, generate a display value or values, among other functions.

As shown in FIG. 1 and FIG. 3, the device is equipped with a wireless transmitter 306, such as those conforming to the Bluetooth™ Smart (also known as Bluetooth™ Low Energy) or ANT™ protocols, by which the locally stored data may be transmitted to another device during or after the completion of an event. The transmitter may also receive wireless communication. In one example, the transceiver operates over the Bluetooth™ Low Energy protocol, which is compatible with iPhone™ and other smart phone technologies and has otherwise been ubiquitously adopted in many areas. It is also possible to use a wireless transceiver that communicates over the ANT™ protocol, a standard adopted and used by many fitness products, or other types of transceivers available now or in the future. It is also possible that some information will not be stored locally but rather transmitted in real-time, depending on how the device is configured, for remote storage, computation, and/or display. Using the open API, devices, such as a smart phone or tablet, may include apps or applications that receive, process, and display the data and derivations thereof. Moreover, such apps may also be used to configure the device, select an activity that controls how the device records data and processes activity information. In the case of activity selection, if the user selects running, the device will record and interpret data knowing the data pertains to the activity of running. Similarly, if the user runs a swimming app that sets a swimming mode within the device, the device will record and interpret the data knowing the data pertains to the activity of repeatedly swimming lengths in a pool. If the device is configured in a riding mode, then various riding protocols, such as riding cadence and riding posture, may be initiated and data recorded and/or transmitted. Activities would be selected through a user interface on a remote device, and the selection wirelessly transmitted to the device.

Unlike a watch or an application running on a smart phone, a user may interact with the device through various possible taps to the device, which taps are detectable by the accelerometer. Namely, rather than pressing a button or interacting with a touch screen, the device may detect and act on taps to the device. In one embodiment, the device does not include any form of display, touchscreen or otherwise, but rather may accept user commands through taps. The device may also be controlled, in real-time or otherwise, by an app in wireless communication with the device, and may present information and user feedback, through LEDs 310 and/or vibration of a vibration motor 308 controlled by the processor (haptic feedback) and/or through information transmitted to and displayed at an app running on a device with a display. Additionally, the device may be controlled with a display and control hub that is configured to operate other devices.

The accelerometer is able to detect taps from a user and the processor is programmed to run different routines based on the number or taps, sequences of taps, or the like. For example, the user can start recording heart rate and other data by tapping the device twice, and may stop the recording through a subsequent pair of taps. In some instances, the device may begin recording heart rate as soon as its detected but will mark the heart rate data when taps are received.

Figure 4:
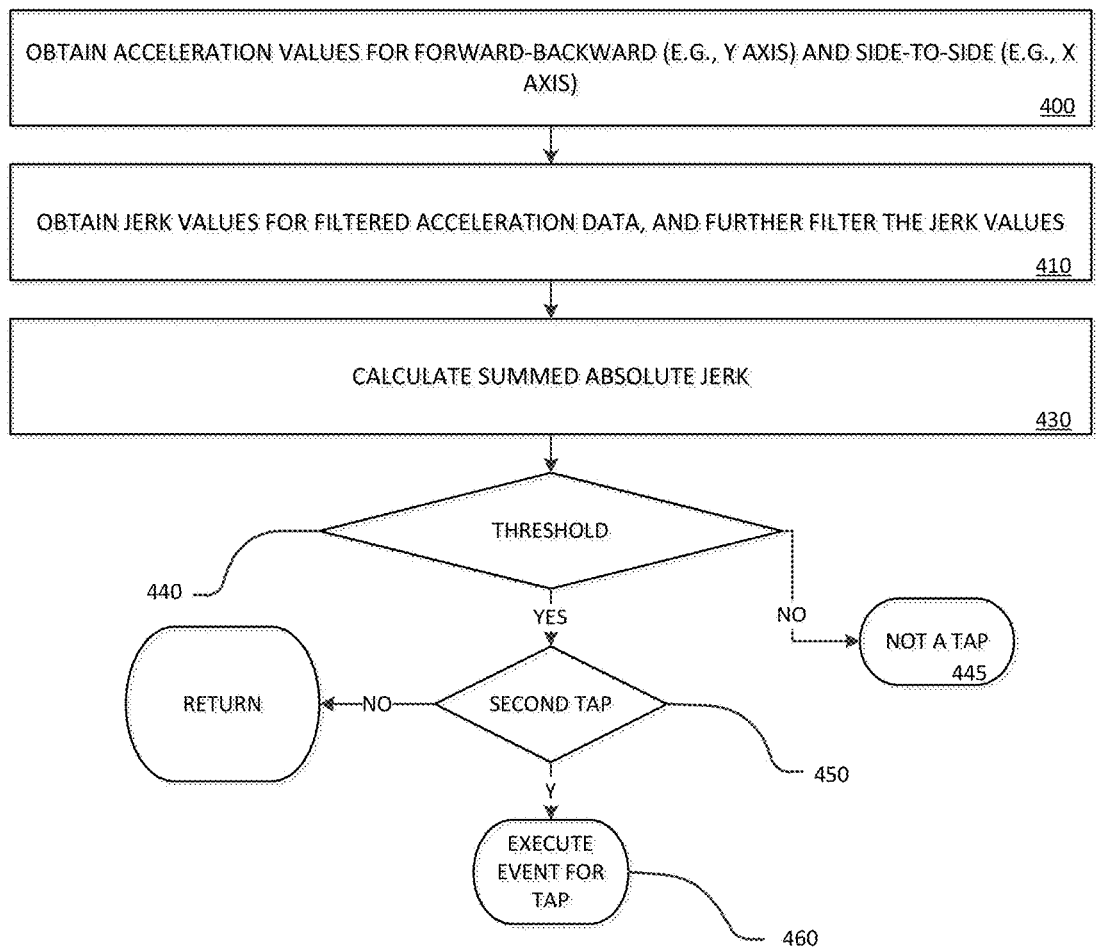
FIG. 4 is a flow diagram illustrating a method of detecting human initiated taps to the activity monitoring device, and executing some action based on the detection of the taps.

FIG. 4 is a flowchart illustrating one possible method of detecting taps and execute some event when a valid tap (or taps) are detected. Taps can be detected from rapid changes in the acceleration signals. Since such rapid changes in acceleration signals are not exclusively triggered by taps, but might also be triggered by other forceful impacts (e.g., landing impact while running, jumping, or bumps while cycling), careful processing is necessary to maximize the number of correctly detected taps while minimizing the number of falsely detected taps. The device is worn in such a way that the accelerometer is able to measure accelerations in the following directions: in/out of the chest→"forward axis" (x-axis), horizontal axis parallel with the surface of the chest→"side to side axis" (y-axis) and the vertical axis parallel with the surface of the chest→"vertical axis" (z-axis).

Referring to FIG. 4, in one specific implementation, a tap might be detected by obtaining derivative values of the accelerations identified in the forward-backward and side-to-side axes (operation 400 and 410). The derivative of acceleration may be referenced herein as "jerk" or velocity. Prior to calculating jerk values, the device may first filter the acceleration data to remove low frequency events as such low frequency events are likely not taps (operation 410). So, for example, the accelerating data may first be processed with a filter.

The process next involves calculating a summed absolute jerk value by summing the absolute forward-backward and absolute side-to-side jerk values (operation 430). The process is looking for a value that accounts for higher frequency accelerations in two dimensions. Intuitively, a tap would involve the user essentially pressing or tapping the device and hence the acceleration data would be identified in the forward-backward axis (x-axis). However, taps are not precise and are typically accompanied by a significant acceleration along the side-to-side axis (e.g., y-axis). Accordingly, the process also includes information from the side-to-side axis. Further, by including two axes, false positive events are more likely discriminated. For example, a jump may be associated with a quick acceleration in the forward and vertical axes but not the side-to-side axes. Such a jump would possibly initiate a false positive if side-to-side jerk values were not considered in conjunction with forward jerk values. A person skipping may initiate numerous tap based events without proper discrimination between a tap and some acceleration event falsely attributed to a tap.

Next, the summed absolute jerk value may be compared to a threshold, and if the tap meets the threshold it is marked as a start of a potential tap (operation 440). If the summed absolute jerk does not meet the threshold, it is not a tap (operation 445). When the summed absolute jerk then crosses a second threshold, it is marked as the end of a tap (operation 430) and the event registers as a first tap. In one implementation, the absolute value first crosses the threshold in one direction (e.g., upward) and then crosses the threshold (or a different threshold) in the other direction (e.g., downward), which collectively indicate a sharp acceleration event, associated with a user initiated tap. In one example, the summed absolute jerk must meet a threshold of 200 G/s to be considered a tap. The system is analyzing the data for a change in acceleration of at least 2G between two consecutive samples. The time between samples is 0.01 second, hence a change of 200 G/s per second, in one example. 200 G/s is simply one example of a threshold value, and other values may also be considered depending on the implementation. Moreover, based on filtering, errors, sensitivity, and the like a range of + or −20 G/s may be allowable and considered as a threshold. The taps may further or alternatively be compared to a time threshold. So, while magnitude of the absolute jerk may be an important indicator of a tap, it is also possible to assess an absolute jerk event with the time duration of the event. In one example, a tap start is identified when summed acceleration exceeds 200 G/s, and an end tap is when the jerk falls below 200 G/s. The collective start and end is registered as a tap. Any or all of the events discussed may be compared with respective thresholds to discriminate between taps and other acceleration inducing events.

To further discriminate non-tap events from taps, the system looks for two tap events before taking any action based on a tap (operation 450). Some form of action may be initiated upon the detection of two taps within a predefined time window (operation 460). The second tap is processed like the first tap: namely, the summed absolute jerk of forward-backward and side-to-side meeting a threshold (e.g., 200 G/s). The second tap is also detected within a time of the first tap (e.g., 110-260 ms) in order to be considered a second tap rather than a new first tap.

As discussed, some features and functions of the device may be controlled by the user tapping the device. In one implementation, the accelerometer detects accelerations and the processor is configured with computer executable instructions implementing the process of FIG. 4. The processor, in turn, may have various possible routines or functional blocks that are initiated, controlled, etc., based upon the detection of a tap or taps. The processor may also initiate communication with a remote device, such as a smart phone. In one possible example, execution of a tap (or double tap as described) initiate a communication to a music app, e.g., Pandora™, Spotify™, iTunes™, or the like, to advance to a subsequent track.

Additionally, the accelerometer can detect the wearer's movement, and more particularly accelerations (decelerations), in three dimensions. The processor interacts with the accelerometer to store the acceleration data. Alternatively, the device may include a 9-axis inertial measurement unit (IMU) which uses a gyroscope and compass in addition to a 3-axis accelerometer. The device may also include an altimeter 312. The IMU would allow the device to detect the orientation of the user on both a local and global scale. The information gathered with the 9-axis IMU could aid in the calculation of running efficiency as well as allow the device to detect slight changes in direction that a 3-axis accelerometer may not be able to recognize. This may allow the device to more accurately detect common exercise movements like sit-ups, push-ups, and the like. The term "accelerometer" as used herein refers to both a 3-axis, a 9-axis, and other devices able to detect acceleration.

Also coupled with the processor is a differential amplifier 308 configured to receive signals from a pair of electrodes 302(A), 302(B). The processor, memory, and other electrical components discussed herein, are encapsulated in a watertight housing 108. The housing is mounted on the adjustable strap 104 that the user may wear around his or her chest. The housing may be fixed to other mechanisms or clothing positioning the device on the user's torso. The electrodes are positioned on the strap and generally positioned so that when the device is worn correctly, the housing is roughly positioned at the base of the sternum and the electrodes to either side generally at the bottom of the pectoral muscles. Alternatively, as shown in FIG. 2, the electrodes are positioned on opposing end regions of the housing 106. The electrodes and housing may be positioned on other locations of the user's torso.

The electrodes detect very small electrocardiographic signals emitted from the heart. Generally speaking, each heart beat is associated with Q, R, and S waves (sometimes referred to as the QRS complex). The R wave signal is most prominent and typically the time between R waves is used to determine heart rate. For example, if an R wave is detected each second, the heart rate is 60 beats per second. Due to the relatively small electrical R wave signal and since the R wave signal is detected with some slight time offset at each electrode, the difference amplifier serves to amplify the R-wave while at the same time rejecting common mode noise. The processor may further be programmed to filter other noise, and detect and count R-wave peaks associated with heart beats. Further, the processor may record the heart rate data in the memory, and/or transmit raw or processed heart rate information to an app for calculation, presentation and/or storage.

Besides being controlled through taps, the device also may include a vibrator 308 that provides various forms of programmable feedback to the person wearing the device. In one possible implementation, the processor, by tracking cadence, can compute distance traveled and provide a vibration each mile or at some other proscribed distance. Similarly, the device can monitor heart rate and provide vibration feedback based on the wearer's heart rate. For example, the user may be training and intending to keep his or her heart rate within or below certain thresholds. The device, such as through a smart phone application (or app), may be set to monitor those thresholds and provide a vibration when the user is within, below or above, the thresholds, among other forms of feedback.

In addition to vibration, the device also may include a pair of LEDs, red and blue for example, or a multicolor LED 310. The LEDs may be controlled and illuminated by the processor based on certain events, such as heart rate detection, or the like. For example, an LED may illuminate when a heart rate signal is detected so that the user knows that the device is detecting his heartbeat. Overall, the device is powered by a battery or batteries, such as a lithium coin style battery.

In order for the device to communicate with an application or app, an API may be running in conjunction with the app so that the app or other apps may communicate consistently with the device. The API will provide an interface to the various possible settable and programmable attributes of the device. Further, the API will provide a format for communicating with the device. So, for example, through the API, an application may be able to set the mode of the device to record or not record certain values, to activate or deactivate certain activities (e.g., running or biking) and thereby cause different possible routines to be executed, to enable or disable certain routines, to enable or disable communication with other devices (e.g., enable real time streaming of values to the application, record certain values, or both) and the like. Generally speaking, the API provides an open protocol so that developers can understand the function of the device, set-up the device to perform various possible functions, communicate with and control the device, and receive information from the device.

Cadence

Figure 14:
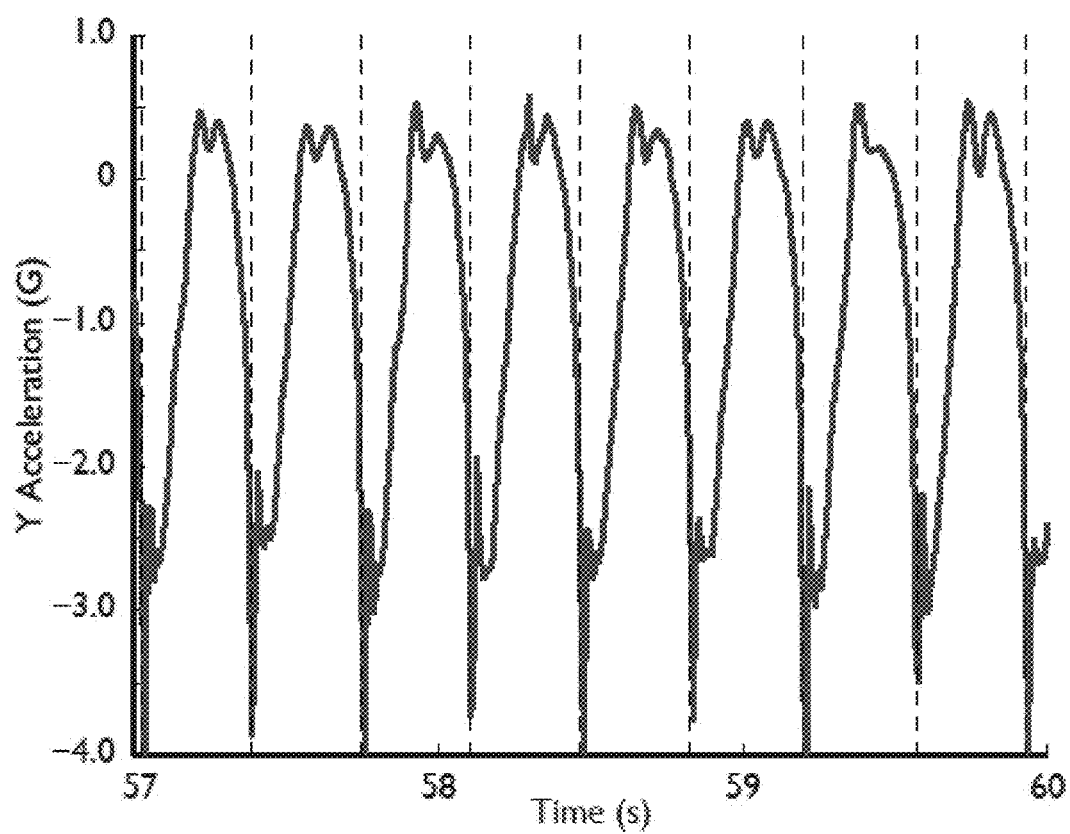
FIG. 14 is a trace of y-axis (vertical) acceleration data for a runner.

Since the device includes an accelerometer, it can detect cadence. Generally, cadence is a measurement of the frequency of a particular action or motion. For running, cadence is the number of times a runner's foot strikes the ground on a per minute basis. FIG. 14 is a trace3 of y-axis (vertical) acceleration data for a runner. In one implementation, running cadence may be derived by analyzing accelerometer data representing the vertical axis in order to detect periodic/repeating signals. In other implementations, accelerometer data collected from other axes could be incorporated into the cadence detection processing/algorithm.

Foot ground strike times are recorded precisely by finding the maximum and minimum occurrences of acceleration in the vertical axis. The foot ground strike coincides with a strong vertical acceleration just after foot impact with the ground during running. The rate of foot strikes determines cadence, which is calculated, recorded and/or transmitted, and also the basis for further analysis. Feedback can be given via the onboard vibration motor or LED's during the activity based on computed cadence.

Figure 5:
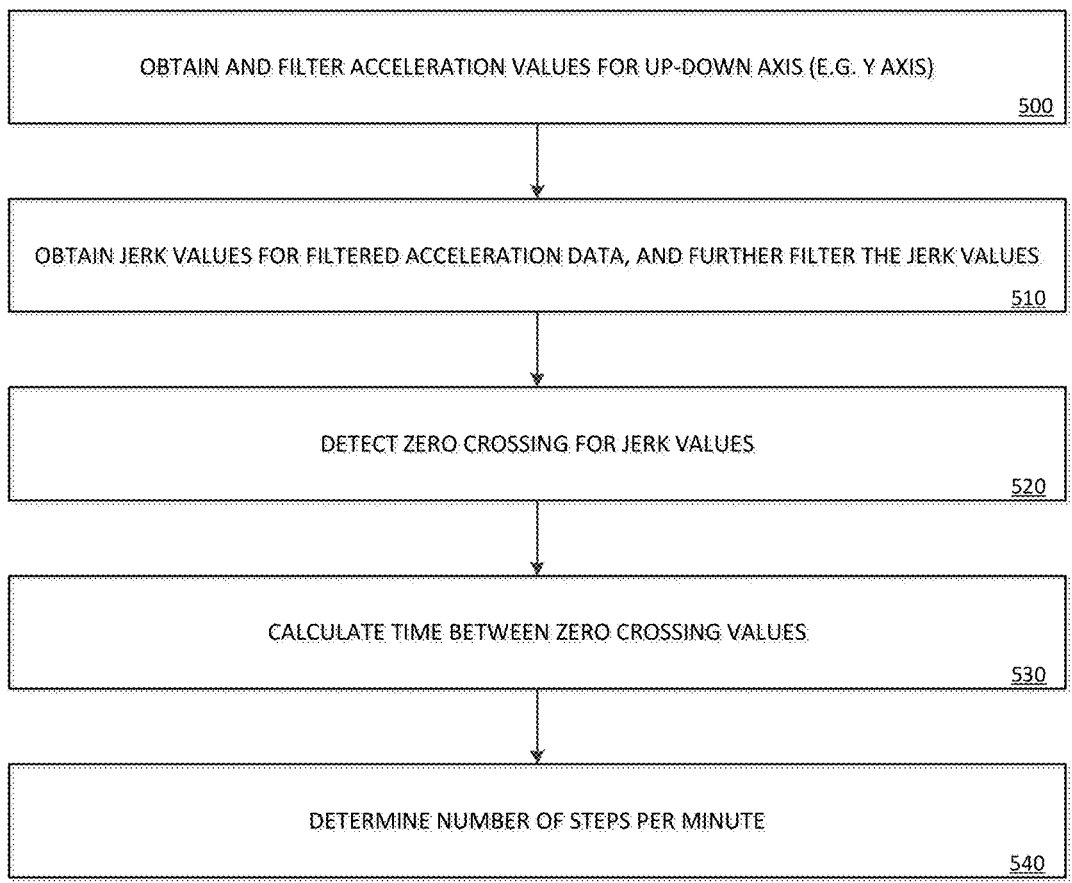
FIG. 5 is a flow diagram illustrating a method of deterring cadence using the activity monitoring device, which includes an accelerometer.

In one specific implementation, the processor may include computer executable instructions sufficient to implement the process illustrated in FIG. 5. More specifically, cadence may be first include obtaining up-down (e.g., vertical or z-axis) acceleration values from the accelerometer. These values may be stored in the memory for processing, or cached and processed in pseudo-real-time (operation 500). The acceleration values may be further processed in a low pass filter, such as a second order Butterworth filter having a cut-off frequency of about 2 Hz. The filtered acceleration data is then processed to obtain a jerk value, such as through a derivative of the acceleration value (operation 510). The process then detects a zero crossing to identify the start of a step. In one example, the system identifies negative going zero crossings and measures the time between each negative going crossing to identify a step (operation 530).

- Each "negative going" zero crossing is detected, which signifies the start of a new step and the end of the previous step
- The cadence value may be compared against various possible thresholds to eliminate erroneous values.

The system counts the number of zero steps for each minute and provides a cadence value (operation 540).

Running Speed and Distance Calibration

Both speed and distance may be calculated from accelerometer data and/or information which has been derived from the accelerometer data. In one implementation, cadence may be used to compute speed and distance. In another implementation, Ground Contact Time (GCT) (the time per step that the runner's foot is in contact with the ground) may be used to compute speed and distance. In a specific implementation, the system may also incorporate heart rate into the speed and distance computation to more accurately calculate speed and distance. Initially, however, the system does not know the runner's step length. A runner's cadence or ground contact time may be relatively consistent at different speeds. However, the runner's step length along with heart rate will increase with an increase in speed. Thus, the system may include one or more calibration methodologies that may be used alone, may be performed in conjunction with a separate application, or some combination thereof. The calibration methodologies may use cadence, ground contact time, raw acceleration values, heart rate, time and some separate and accurate reflection of distance traveled to calibrate speed and distance measurements by the device.

In one implementation, the user will enter a calibration mode through tap selection or by way of an application in communication with the device through the API. With respect to the use of an app, the user will access the app on a smart phone, tablet or the like, and will select calibration mode. The app (built using the API) will communicate the selection to the device by way of Bluetooth™ Smart (also known as Bluetooth™ Low Energy) or ANT™ wireless communication, and cause the device to enter calibration mode. Once in calibration mode, there are several possible ways to calibrate the device. In one example, the user will run with both the device and an app running on a separate device where the app determines and records distance and speed using GPS or other methods. During or at the completion of a run, the device downloads data derived from accelerometer data such as cadence, ground contact time, vertical oscillation etc. and heart rate data to the app. In turn, the app either directly or using a remote server, compares the GPS based speed and distance values with the downloaded data values to create calibration values.

In another possible implementation, the user will run at a series of set speeds at a set distance on a treadmill, on a track or some other course where distance is accurately measured. During or at the completion of each speed set, the device downloads data derived from accelerometer data such as cadence, ground contact time, vertical oscillation etc. and heart rate data to an app. Then, either the app, a remote server or the device itself will calculate calibration values. In this example, a user may enter known values at a user interface. The user can follow instructions from the connected app to perform the calibration. The app may, for instance, ask the user to run at several different constant speeds, automatically recording the data from the sensor during the effort. At the end, the collected data is utilized to generate relationships between transmitted data and speed.

Speed and Distance from Ground Contact Time

In an alternative implementation, speed and distance may be calculated from ground contact time. The process of calculating speed and distance from ground contact time is similar to the method that is described for cadence. Generally, a regression equation between ground contact time and speed is used. Specifically, a second-order regression equation may be used.

The regression equation may be tailored or customized for each user. In one specific implementation, it is possible for a user to use one of two different methods to determine their regression equation. In the first method, users run on a treadmill at a few different speeds (e.g., an 'easy pace', a 'moderate pace', and a 'fast pace') for two minutes each (or some other time). The regression equation may then be calculated from the user-entered speeds and measured ground contact times (discussed below). In the second method, users only have to run at one speed ('preferred pace') for two minutes, still on a treadmill. The measured ground contact time and user-entered speed are then used to 'correct' a default regression equation, by adjusting the offset of the default regression equation so it intersects the single recorded ground contact time-speed combination. The default regression equation is the average regression equation for a number of different runners, and is hard-coded into the device.

The general form of the second order regression equation is (speed is running speed in meters/second, GCT is ground contact time in seconds, b1-b3 are the regression coefficients):

$$speed = b1 * gct^2 + b2 * gct + b3$$

In a specific example the default regression coefficients could be as follows: b1=135, b2=−97 and b3=19.

Now say that the a user performs a one-point calibration which results in an average ground contact time of 0.26 seconds at a speed of 3.25 m/s. Using this ground contact time, the default regression equation would have estimated a speed of $135*(0.26)^2 + -97*(0.26) + 19 = 2.90$ m/s. The error is thus 3.25−2.90=0.35 m/s. The regression equation would be corrected by adjusting the offset (b3) by this error—the new regression coefficients would be b1=135, b2=−97 and b3=19.35. Effectively, this correction shifts the default calibration equation up or down to ensure that the relationship goes through the GCT-speed combination found in the one-point calibration. It has been found that generally the shape of the relationship (determined by b1 and b2) is somewhat constant between runners and most of the variability is in the offset (b3), correcting the default relationship by adjusting the offset leads to good results for most people.

If users do not calibrate their device, the default regression equation is used to calculate speed and distance.

Running Efficiency

One of the benefits of the device is that the user wears it around the chest, as opposed to in a foot pod or a wrist bracelet, for example. This placement allows the device to provide more accurate information about the movements of the user's center of mass. Generally speaking, a runner is most efficient when they are not wasting energy producing redundant and/or excessive forces. Such forces would result in redundant and/or excessive accelerations—and thus movements—of the user's center of mass, and would be reflected in the acceleration signals captured by the chest worn device. Assuming a user runs on flat ground, the goal of running is to progress forwards. Although, paradoxically, some movement in planes orthogonal to the direction of progression improve running efficiency—this is due to the physiology and mechanics of the human body—redundant and/or excessive movement in these directions would reduce efficiency. Examples of such movements would be excessive vertical movements, or ineffective side-to-side movements. Referring to the side to side axis, if the user is periodically or intermittently accelerating along this axis, then the runner is moving from side-to-side, limping, favoring a leg due to some form of injury or otherwise is injecting an inefficiency into their forward motion by using some of their energy to move and stop movement to one or both sides rather than forward. With respect to the vertical axis, if there are accelerations along this axis then the runner is translating some of their forward movement to moving the body upward. Similarly, the runner must expel some energy to support the body as the runner lands from the upward movement. Both of accelerations and decelerations along the vertical axis waste energy.

Finally, and perhaps the most impactful, some runners, through overextending the leading leg during their normal stride, inadvertently impart excessive braking into their stride. This is commonly referred to as "overstriding". Generally speaking, when a runner overextends their leading leg a momentary braking effect occurs when the foot strikes the ground. This braking effect translates into a deceleration along the direction of travel Assuming a runner's stride is relatively symmetric, then these decelerations are detected for each stride and at a relatively periodic interval that matches with the runner's cadence. One way to reduce the braking effect is to shorten your stride. To maintain speed relative to a longer stride, it is necessary to also increase cadence proportionally to the shortening of the stride. Besides the braking effect, shortening or otherwise optimizing stride length can help reduce the frequency or severity of various possible injuries. It is also often the case that a shorter stride length naturally leads to less vertical up and down movement. Overstriding and the braking effect also may be seen in decelerations along the vertical axis caused by the runner landing on their heel and decelerating during the landing.

Some or all of the acceleration data detected by the accelerometer may be used to calculate a running efficiency metric. Additionally, the different forms of accelerations may be weighted in order to reflect their importance on overall running efficiency. The device may measure movement from side to side (away from the centerline and then back to the center and then to the other side), upward movements differentiated from landings, and forward strides differentiated from decelerations due to braking, among other things, from the 100 Hz three axis accelerometer data. For instance, a forward stride deceleration would show in the forward axis accelerometer data, but would not have much effect on side to side axis accelerometer data.

Through some form of user input/interaction, the runner may also initiate the use of different running efficiency metrics or isolate the metrics. In one implementation this user interaction may take the form of tap detection. In another implementation, a connected smart phone app could be used for the interaction. So, for example, the device may default to a running efficiency that accounts for each of the dimensions measured. The runner, however, may initiate different routines that focus on or isolate the distinct metrics. Thus, a runner focused on increasing cadence and shorting stride length, may initiate a routine that only reports forward accelerations and decelerations, vertical accelerations and decelerations, or a combination of only these measurements. A diagnostic metric may focus more on side-to-side movements or non-symmetrical braking (one leg braking more than the other) and comparisons over time as a runner, whether knowingly or not, will favor one leg or another, which accompanies a more dramatic side-to-side movement as opposed to when not nursing an injury, and/or more dramatic braking of one leg relative to the other. Such data may be especially helpful to a coach who may not know that a runner is developing an injury, and may help that coach detect the early onset of an injury and avoid it from worsening.

In one implementation, the running efficiency metric is as follows:

$$RE = X1(\text{forward-deceleration}) + X2(\text{side-to-side-acceleration}) + X3(\text{vertical-acceleration}) + X4(\text{vertical-deceleration})$$

Where: $X1$=braking factor, $X2$=side-to-side factor, $X3$=vertical acceleration factor, and $X4$=vertical deceleration factor.

Each of the elements of the Running Efficiency (RE) function impart some degree of running inefficiency; hence, a lower number is generally associated with a better and more efficient running gait, while a larger number, where the runner has larger accelerations or decelerations in each of the categories, is associated with a less efficient running gait. Of course, these numbers can be presented in other forms so that the displayed value is understandable. By lowering their RE number, a runner can realize and track improvement in their running efficiency. The factors are weightings to maximize or minimize (control) the effect of any given element on the overall running efficiency metric. For example, to emphasize the braking element over the side-to-side element in the overall RE metric, the X1 factor is set to a larger number than the X2 factor. It is also possible to normalize the RE number range to some range between 1-10, or 1-100, or some other range, where a 1 in either range would reflect the most efficient calculated running efficiency. Overall, the RE number accounts for acceleration data from the three measured directions/axes and allows for weighting of values in each measured direction to account for the relative importance, if any, to the effect of measurements along each direction and the determination of overall running efficiency.

Moreover, improvements in the running efficiency metric may be used to help a runner understand how their stride and form is improving, what is working and what is not, and the like. Aspects of the present disclosure may also be directed at running smoothness. While similar to efficiency, differences in calculation techniques using x, y and z axis acceleration data provide different resultant numbers and hence are referred to herein using efficiency and smoothness.

Running Smoothness Based on Jerk Cost

Running smoothness may be captured through a "jerk cost" measurement. Generally speaking, research indicates that movement, such as walking, jogging and running, can become smoother with practice. Hence, quantifying smoothness and providing a mechanism by which a person may objectively identify improvements in smoothness can provide indications that sustained exercise is providing objectively quantifiable improvements. Furthermore, providing quantitative feedback regarding smoothness might encourage runners, or other athletes, to modify their running technique, or other movement technique, in an attempt to improve their smoothness. Smoothness reflects a quantification of the observation that people tend to move smoothly as they become stronger, more proficient, and/or trained in their movement. Thus, smoothness may allow an athlete to correlate performance with an objective metric (smoothness). Moreover, as discussed below, an athlete may compare their smoothness with those of others through correlation or comparison to average smoothness values of other athletes.

Figure 6:
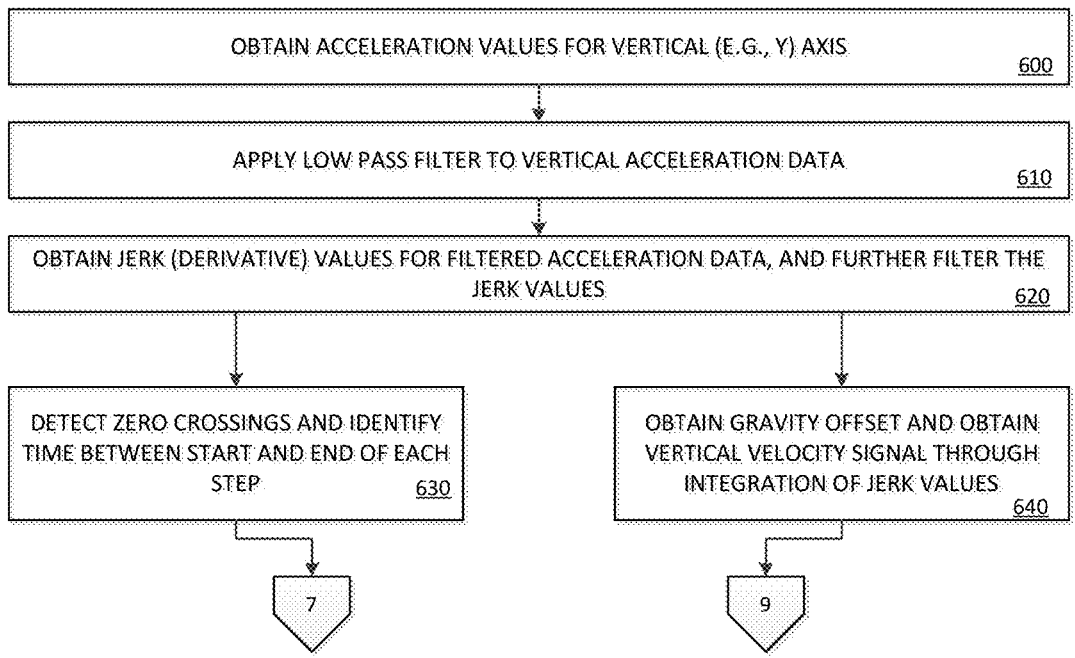
FIGS. 6 and 7 and 6 and 9 are flow diagrams of a method of generating a running smoothness value based on measurements of the activity monitoring device and a method of calculating vertical oscillation based on measurements from the activity monitoring device.
Figure 7:
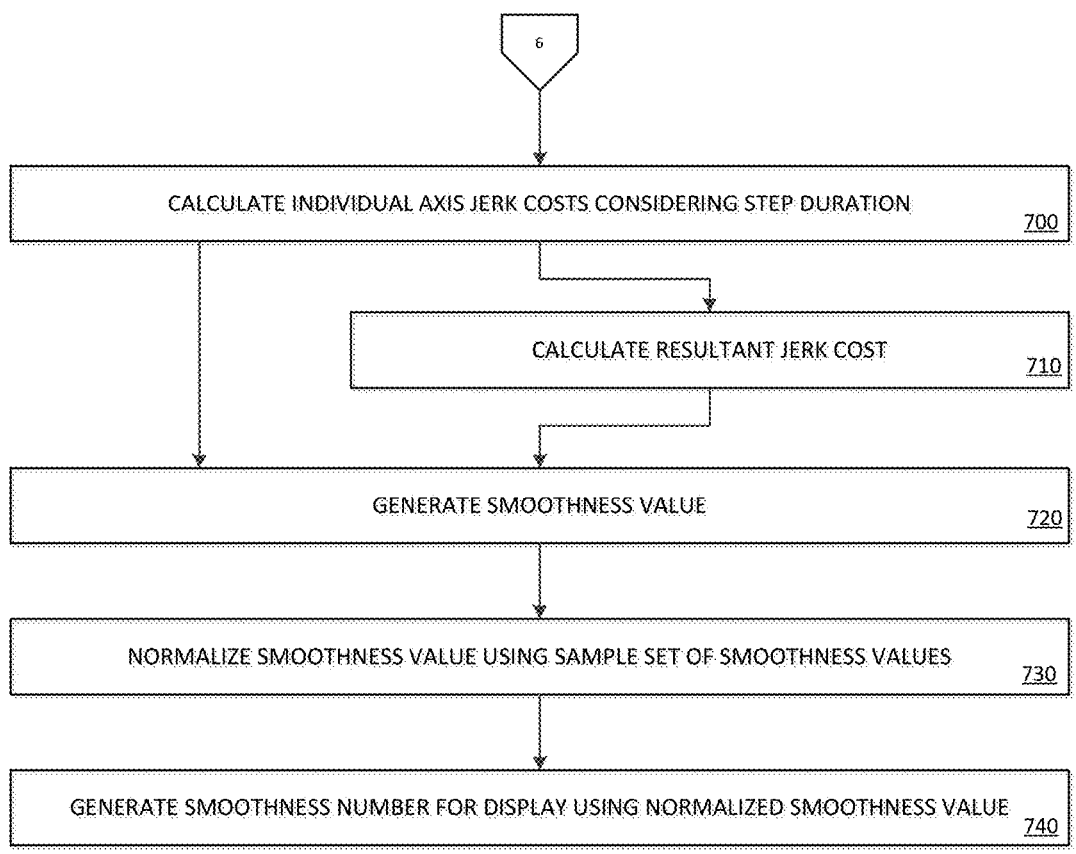

FIGS. 6 and 7 illustrate one possible method of obtaining a smoothness value, which may be displayed, stored, and used in further calculations, and the like. To begin, the smoothness calculation involves obtaining and filtering each axis of acceleration data (operation 600) and then obtaining jerk values for each axis of acceleration data (operation 610). In one example, the system takes into account acceleration values from side-to-side, vertical and forward-back movements. In one implementation, the acceleration signal might be filtered prior to calculating the derivative, for example using a 25-Hz second-order Butterworth filter. Jerk is calculated as follows:

$$\text{jerk} = \frac{d(\text{acceleration})}{dt}$$

The calculation centers jerk around the zero axis. The system may then detect zero crossings and calculate the time between each crossing (operation 630). Jerk cost may then be calculated as the time integral of the squared jerk for each step, normalized by the duration of the step (FIG. 7, operation 700):

$$\text{jerk cost} = (\int \text{jerk}^2 dt)/\text{step duration}$$

The jerk cost measurement captures the rate of change of acceleration ("jerk"). By using step duration, the jerk cost eliminates the effect of longer steps on the jerk calculation. Essentially, longer steps might normally result in a higher jerk cost. Accounting for step duration removes that effect on the jerk cost calculation. To calculate jerk cost, the integral of the square of the derivative of acceleration is captured at the conclusion of each step and divided by the step duration (time between foot contacts), and the integral (sum) is then reset in preparation for processing the next step. The jerk cost may be calculated separately for each axis contained in the accelerometer. If one axis of data is being used to calculate smoothness, then the process proceeds to generating a smoothness value (operation 720). Alternatively, if two or more axes are used to generate a smoothness value, then the system first generates a resultant jerk cost (operation 710). The device being worn may stream the jerk cost value(s), and the receiving device may calculate the running "smoothness" metric. It is also possible for the worn device to calculate and stream the calculated smoothness metric.

Figure 8A:
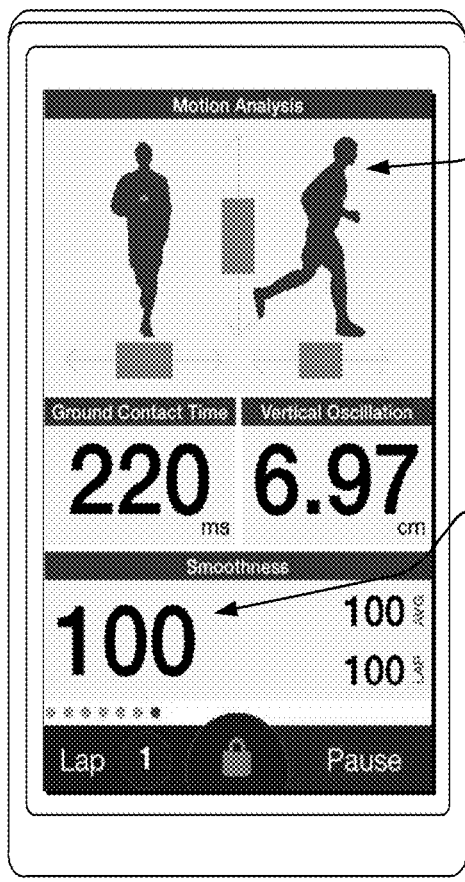
FIGS. 8A and 8B are example graphical user interfaces including displays of various metrics generated from measurements and methodologies disclosed herein.

In one implementation, the z-axis of the accelerometer is oriented in the forward direction of travel, the x-axis is oriented to capture side-to-side movement, and the y-axis is oriented to capture vertical movement. In such an arrangement, the jerk cost(y) value captures the smoothness of vertical foot striking—the higher the value the more jerky the vertical foot strike, the jerk cost(z) value captures the smoothness of braking and acceleration in each step, and the jerk cost(x) value captures the smoothness of side-to-side movements. As shown in FIG. 8A, these values may be graphically depicted relative to a pair of runner graphics.

In such an implementation, the jerk cost values for the separate axes can be combined by calculating a "resultant jerk cost" prior to calculating the smoothness metric, to allow for presenting a single smoothness metric incorporating smoothness in all dimensions. In one example, the resultant jerk cost is obtained as follows:

$$\text{Resultant Jerk Cost} = \text{square root}(\text{jerk cost}(x) + \text{jerk cost}(y) + \text{jerk cost}(z))$$

Normalization would usually involve squaring the values being added for the square root calculation. However, in one implementation, the jerk costs values are not squared prior to the square root as squaring is accounted for in the jerk cost calculation. In a different implementation, the resultant jerk cost could be calculated directly from a resultant acceleration (calculated as the Euclidean norm of the acceleration vector: $|a| = \text{square root}(x\text{-acceleration}^2 + y\text{-acceleration}^2 + z\text{-acceleration}^2)$).

In one specific example, a raw smoothness value may be calculated as the inverse of the jerk cost, so that smoothness increases when jerk cost goes down (or vice versa) (operation 720) and is calculated as follows:

$$\text{Smoothness} = 1/(\text{Jerk Cost})$$

In this example, jerk cost may be resultant jerk cost or the jerk cost value for one axis.

Alternatively, the system may further process the data before displaying a "smoothness" number. In one implementation, the system includes a table of expected resultant jerk costs at different running speeds and normalizes the smoothness number using the table data (operation 730). The expected resultant jerk costs are based on raw resultant jerk cost calculations from a sample set of runners at various speeds. The range of values at each speed is averaged to provide an expected resultant jerk cost at each running speed. The resulting number ('normalized resultant jerk cost') is the difference between the average resultant jerk cost (of the sample) and the current users resultant jerk cost at the current speed, as calculated from the equations set out above. If the runner is smoother, their resultant jerk cost is lower at the current speed. Conversely, if the runner is less smooth, the resultant jerk cost is higher. Normalization also, and contemporaneously, normalizes the effect of speed in the smoothness calculation. Generally speaking, as a person runs faster, their jerk costs increase. Hence, without some form of normalization, a runner's smoothness number would reflect less smooth movement as they run faster. Comparing and adjusting using the table values as discussed, normalizes the data for speed. Finally, the normalized resultant jerk cost is transformed into a smoothness number (operation 740).

"Smoothness" may be presented in various possible ways. In one specific implementation, smoothness is presented on a scale where a value of 100 represents an average smoothness, with higher values being smoother and lower values being less smooth. The transformation from calculated normalized resultant jerk cost to the presented smoothness number may include the following steps:

Normalized residual jerk cost is expressed as a fraction of the expected range ($F_{jc}$) based on the sample data.

Smoothness percentile ($F_s$) is calculated as $1-F_{jc}$.

Presented smoothness is calculated as the minimum smoothness value+$F_s$*smoothness range (In the current implementation the minimum smoothness value is 50, and the smoothness range is 100%. The presented smoothness value for the example would then be 50+0.3*100=80).

Running smoothness based on jerk cost measurements may provide information as to how forceful a runner strikes the ground, may provide information as to whether or not the runner lands with an overextended knee (straight leg), may provide information concerning braking and acceleration (along direction of running), and/or the degree to which a runner wobbles (side-to-side). A changing jerk value over time may suggest various possible factors such as fatigue (during a run if the jerk values rises, it may suggest the runner is fatigued and becoming less "smooth" in his or her running form). A changing jerk value over several runs may suggest a runner is dealing with long term fatigue or the runner's shoes are becoming worn and providing less cushion.

Display

Figure 8B:
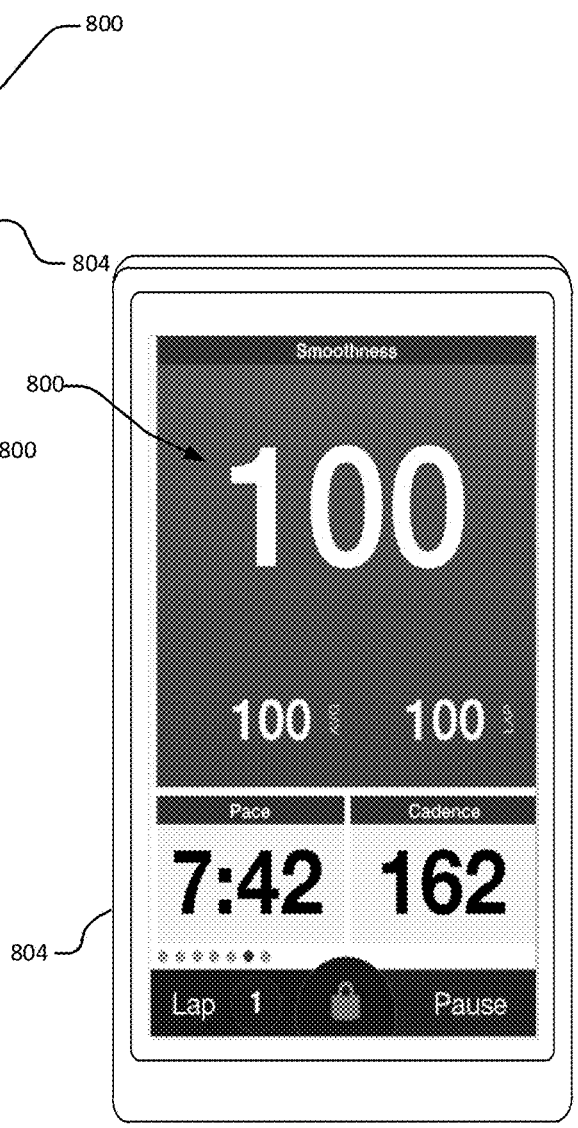

FIGS. 8A and 8B are graphical displays, which are shown as screen displays of a mobile device 804, one two possible ways of displaying and otherwise presenting information in a mobile environment. In these examples, smoothness 800 is presented as a discrete number (e.g., 100) with a heading "Smoothness," which is also presented adjacent to an average value over the course of a run and a value for a lap. Referring to FIG. 8A, similarly, Vertical Oscillation and Ground Contact Time are presented. Also, since individual jerk values are transmitted, the device may calculate a display with graphic depictions of x, y and z jerk. Here, bars 806 (a, b, c) are presented along the x, y and z axis, and the bars are color coded. If the individual jerk calculation falls within an acceptable threshold, the bars are colored green. If the jerk falls within a range, then yellow may be displayed (indicated more jerk and less smoothness) and finally, if jerk falls outside the range, then the red may be displayed. Similarly, the size of the bar may be an indicator of the jerk magnitude. In the illustrated example, each x, y and z bar is of a slightly different width indicating more or less jerk for each dimension with a larger width indicating relatively larger jerk. In FIG. 8B, Pace and Cadence are presented.

Vertical Oscillation

The device may also be configured to calculate vertical oscillation and/or collect and transmit data for calculation of vertical oscillation. Generally speaking, vertical oscillation is a measurement of the user's upward travel from ground during each step. Since the accelerometer obtains acceleration data measured in m/s$^2$, the second derivative of an accelerometer measurement provides distance in meters. Alternatively, vertical oscillation may also be calculated without the second derivative, which helps reduce errors introduced into the determination from the second integral.

Referring again to FIG. 6, generally speaking, obtaining a vertical oscillation value, whether with or without the second derivative involves first obtaining a vertical velocity value. Accordingly, the system may first capture vertical acceleration values between the start and end of a step (operation 600). The system may then apply a low pass filter or otherwise filter the acceleration values and calculate velocity (operations 610 and 620). Because a component of the vertical acceleration signal is attributable to gravity, the system removes the gravity factor by obtaining a gravity offset prior to integrating the acceleration signal to obtain velocity. In one possible implementation, the gravitational constant (9.81 m/s2) may be used. The system then obtains a vertical velocity signal removing the effect of gravity (operation 640). In one specific implementation, the system integrates y-axis vertical values (less y-axis offset) to yield the vertical velocity signal.

As mentioned above, the process may then obtain the derivative of the velocity signal to yield a vertical displacement signal in meters. Such approach, however, can be sensitive to the quality of the "y axis offset" gravitational value. Alternatively, to avoid the second derivative, the determination of vertical oscillation may instead involve an approximation/assumption that the vertical velocity signal is a sinusoidal signal, and the sinusoid is then the basis of identifying vertical oscillation.

Figure 9:
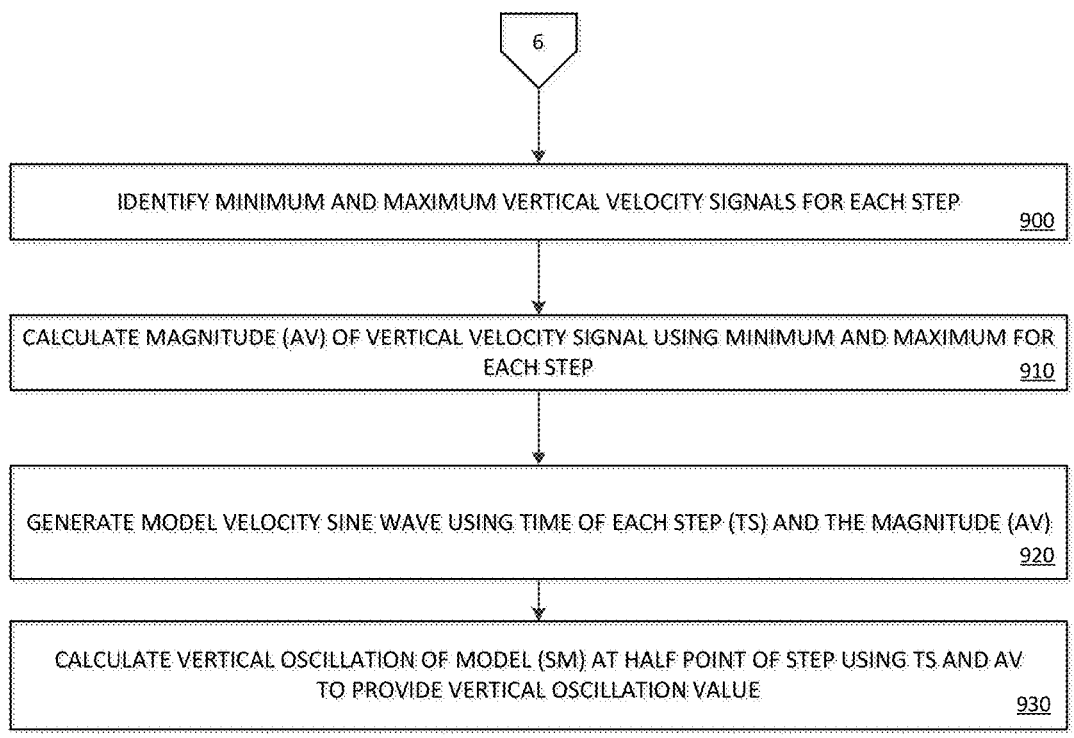

Referring now to FIG. 9, to avoid a second derivative and the error introduced thereby, the system determines a minimum and maximum (peak values) velocity values for each step (operation 900). Next, the system obtains a magnitude of the peak-to-peak vertical velocity signal (Av) (magnitude of the difference between minimum and maximum values, the magnitude divided by 2) (operation 910). The value obtained may be equated to a magnitude of a velocity sine wave.

The system now proceeds to generate a model sine wave from which vertical step height may be determined (operation 920). Generally speaking, the system computes a displacement value at the point in time half way through a step—or at 180 degrees (pi radians) on the model velocity sine curve (operation 930). The computation for vertical height is Sm=(Av/pi) Ts. Here, Av is the peak-to-peak magnitude described above, and Ts is the step duration (time between zero crossing of the vertical velocity signal). The derivation of the calculation and an illustration of why it allows for avoiding the second integral is as follows.

To begin, a velocity sine curve is modeled as follows:

V[t]=Av·sin((2·pi)/Ts)·t) where Av is the magnitude of the velocity sine wave, and Ts is the duration of the step (time between zero crossing), in seconds.

Let k=((2·pi)/Ts), thus velocity sine wave=V[t]=Av·sin (k·t)

The indefinite integral of the velocity sine wave gives the formula for the displacement wave/curve: S[t]=−(Av/k)·cos(k·t)

Taking the definite integral of V[t] from t=0 to t=Ts/2 is given by: S[Ts/2]−S[0]

Thus, the displacement at t=Ts/2, which is the maximum displacement for the step (Sm) is given by the equation: Sm=2·(Av/k)

Expanding k and cancelling "2"s gives: Sm=(Av/pi)·Ts

So, at the conclusion of each step, a new vertical oscillation (maximum vertical displacement) value is computed. This value is fed into a low pass filter or is otherwise filtered. The corner/cutoff frequency of the LPF may be 3 Hz (assuming a 3 Hz sample rate). Once the value is fed in, the latest LPF output is displayed and/or stored as the instantaneous vertical oscillation value. FIG. 8A illustrates one way the Vertical Oscillation value is displayed on a smart phone device.

Generally speaking, the vertical oscillation is the upward component of travel (or may also be only the downward component) but does not encompass both the up and down travel. Vertical oscillation for a chest worn device is the distance travelled vertically (of the chest) from lowest part of step to the highest part of the step.

Ground Contact Time

The device may also calculate and/or transmit data sufficient to calculate ground contact time. Generally speaking, ground contact time is the amount of time that a runner's foot is on the ground during each step. At a high level, ground contact time is calculated by subtracting the time the runner spends in the air form the total step time (time between consecutive foot strikes). During each step, there is period of time when the runner's rear foot has left the ground and the runner's forward foot has not touched the ground. The step time is calculated using raw vertical (e.g. y) accelerometer values, filtering the values with a low pass filter, and taking the derivative of the accelerometer values. The derivate accentuates zero crossing values, which are used to detect the start and end of each discrete step. Step time is calculated as the time between relevant peaks. Air time is calculated using vertical (e.g. y) acceleration values above 0. Essentially, whenever acceleration is at or above 0—without compensating for gravity—the runner is in the air. The vertical acceleration values may be filtered using a low pass filter to improve the detection of air time. In one implementation, the low pass filter may have a cutoff frequency of 5 Hz.

Cycling Cadence

Figure 15:
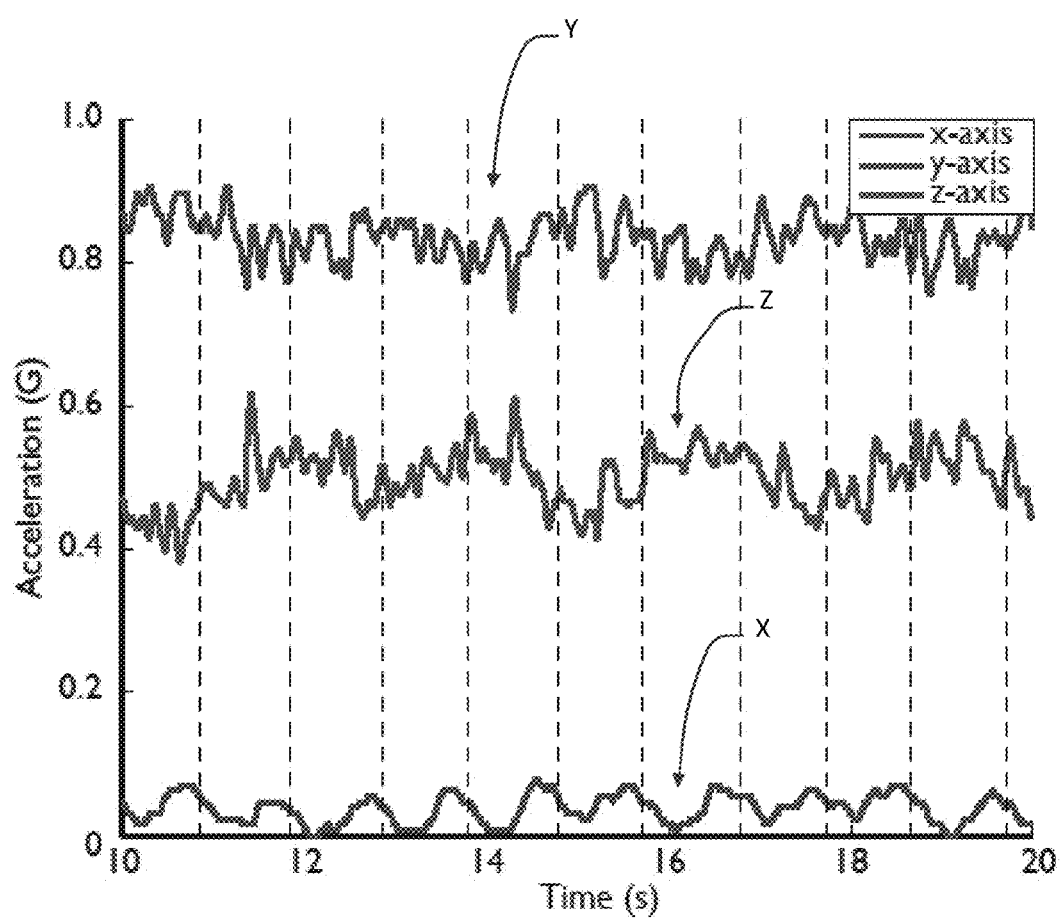
FIG. 15 illustrates traces of x, y and z axis acceleration data for a cyclist, the traces illustrating that the axis most suitable for cadence detection varies (here X), and to illustrate that the oscillations in y/z axis occur at twice the cycling cadence.
Figure 16:
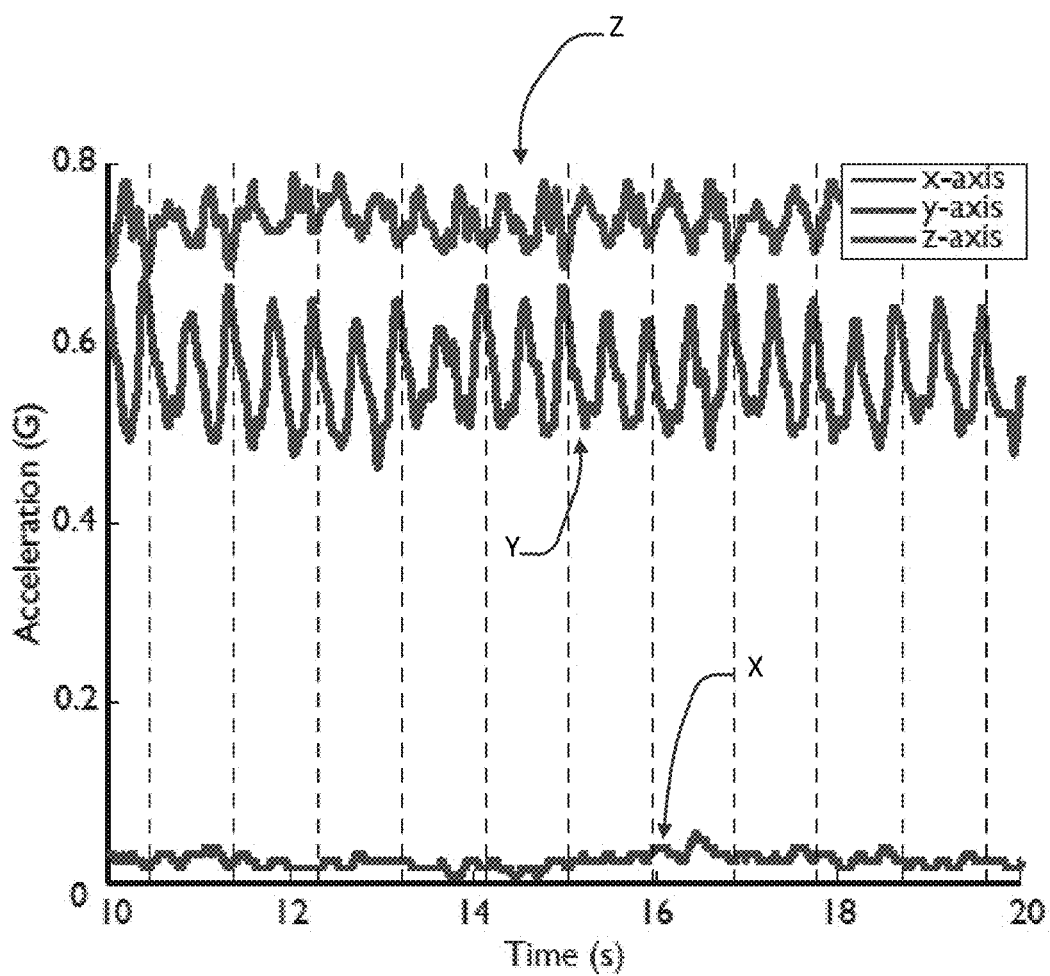
FIG. 16 illustrates traces of x, y and z axis acceleration data for a cyclist, the traces illustrating that the axis most suitable for cadence detection varies (here y), and to illustrate that the oscillations in y/z axis occur at twice the cycling cadence.

Cadence during cycling is defined as the number of crank revolutions per unit time, and is usually expressed as the number of revolutions per minute (rpm). In one implementation of the device described herein, cycling cadence is detected from rhythmic trunk (chest) accelerations resulting from the repetitive motion of the legs when pedaling. In one possible implementation, cycling cadence is detected from the side-to-side, forward-backward or up-down accelerations. However, extensive experimentation shows that the rhythmic trunk accelerations due to leg motion are more or less present in specific directions (axes) dependent on, at least, the user, user position on bike (e.g., hand position on handle bar, as well as sitting or standing position), cadence and intensity. FIG. 15 illustrates traces of x, y and z axis acceleration data for a cyclist, the traces illustrating that the axis most suitable for cadence detection varies (here X), and to illustrate that the oscillations in y/z axis occur at twice the cycling cadence. Similarly, FIG. 16 illustrates traces of x, y and z axis acceleration data for a cyclist, the traces illustrating that the axis most suitable for cadence detection varies (here y), and to similarly illustrate that the oscillations in y/z axis occur at twice the cycling cadence. To deal with this variability, in another particular implementation, the device detects cycling cadence on multiple axes simultaneously, and automatically select the axis which, at the current time, delivers the most reliable cadence estimate.

Figure 10:
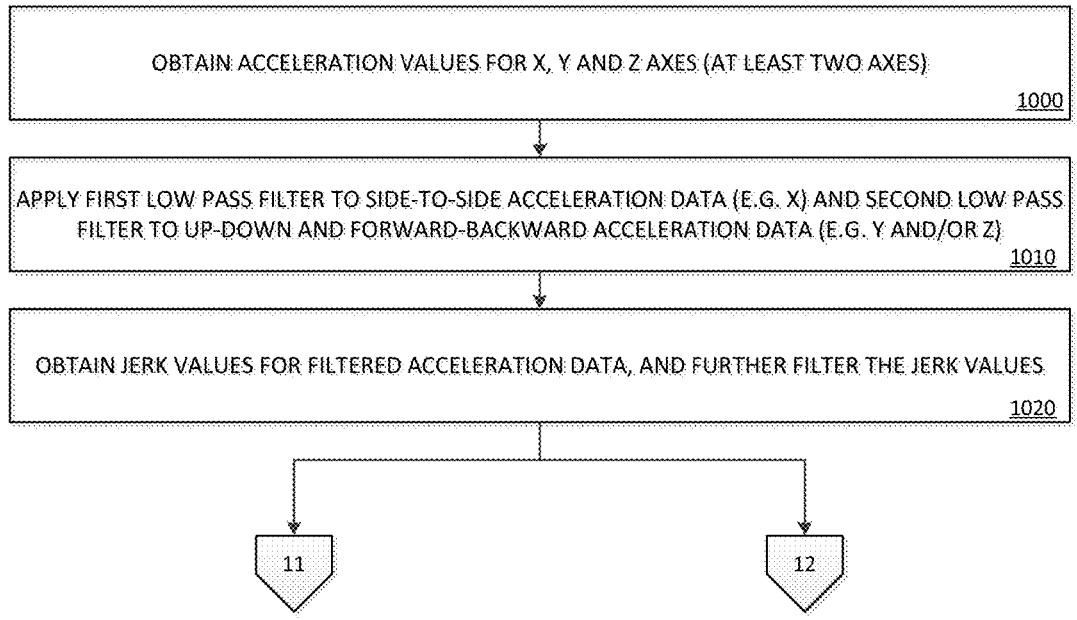
FIGS. 10 and 11 and 10 and 12 are flow diagrams of a method of generating a cycling cadence value from a torso worn activity monitoring device and a method of determining whether a cyclist is standing or seated while riding.

Referring first to FIG. 10, in one specific implementation, cycling cadence may be calculated by first obtaining raw acceleration values for each axis (operation 1000) are fed into a low pass filter (LPF) (operation 1010). In one specific implementation, the LPF may have a corner/cutoff frequency of 1.5 Hz for the side-to-side axis, and 3 Hz for the up-down and forward-backward axes (the repetitive leg motions results in rhythmic trunk accelerations at double the cycling cadence frequency in the up-down and forward-backward direction, hence the doubled cutoff frequency). Next, the derivative of each LPF output is taken to calculate the jerk in three directions (operation 1020). This effectively high pass filters the acceleration signals, removing the steady state offset. The jerk values for each axis are fed into a LPF. These LFP's might have corner/cutoff frequencies similar to the acceleration LPF's.

Figure 11:
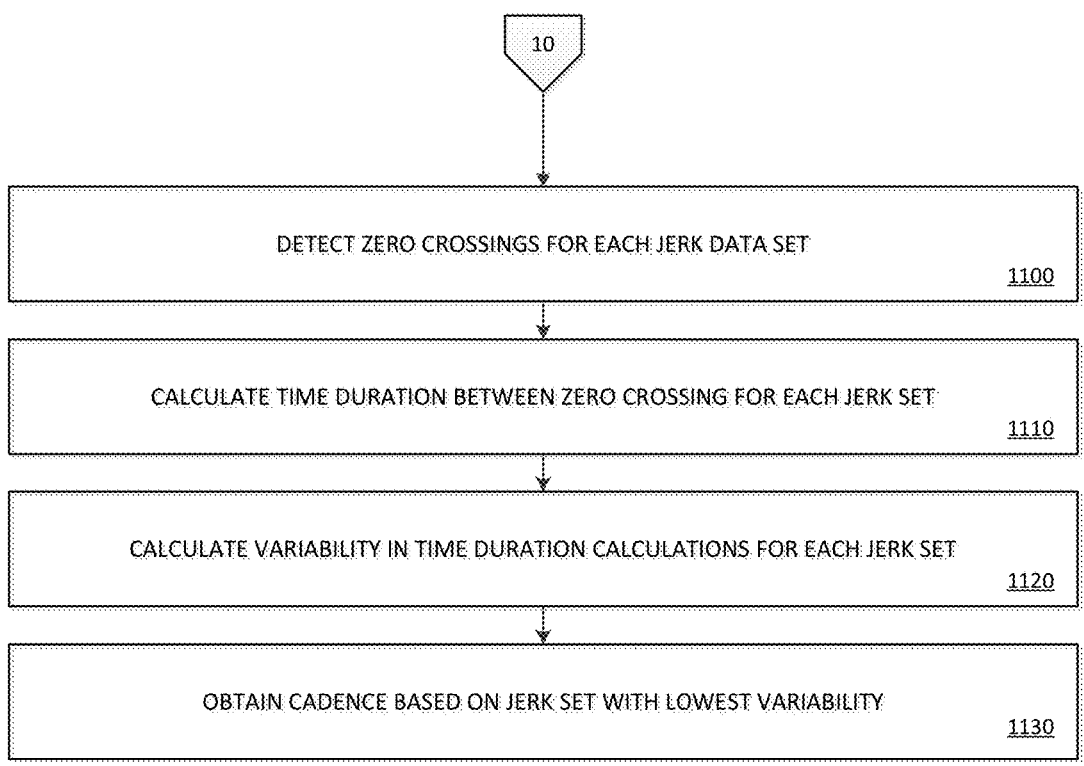

Referring now to FIG. 11, next, the system detects zero crossings for each jerk data set (operation 1100). Each upward ('positive going') jerk zero crossing is detected for each axis, which signifies the start of a new rotation (side-to-side axis) or half rotation (up-down and forward-backward axis).

Each zero crossing is evaluated using a set of criteria (which may include time since last crossing, jerk range between last and current crossing relative to previous signal magnitudes, jerk range relative to an expected range given the current rotation duration, etc.) to remove erroneous crossings. More specifically and in one implementation, the time durations between zero crossings are calculated for each data set (operation 1110). Time duration is calculated between each pair of consecutive upward crossings (side-to-side axis), or each pair of crossings two apart (up-down and forward-backward axis). This duration reflects an estimate of the instantaneous crank rotation duration (1/cadence) for each axis.

The system then determines the variability in time duration calculations for each jerk set (operation 1120). The axes with the lowest variability is chosen to deliver the cadence value. The variability in estimated crank rotation duration over a specified number of rotations is calculated for each axis separately by computing, for example, the range in crank rotation durations for each axis. So, for example, the system will calculate the variability of a rolling set of 5 time duration values for each axes, and will then calculate cadence using the axis providing the lowest variability in crank rotation duration. Instantaneous crank rotation durations may be fed into a moving average filter, which may average the last 5 crank rotation durations, to reduce noise. Cycling cadence is calculated as the inverse of the filtered crank rotation duration (operation 1130).

Cyclist Position (Standing or Seated)

Figure 12:
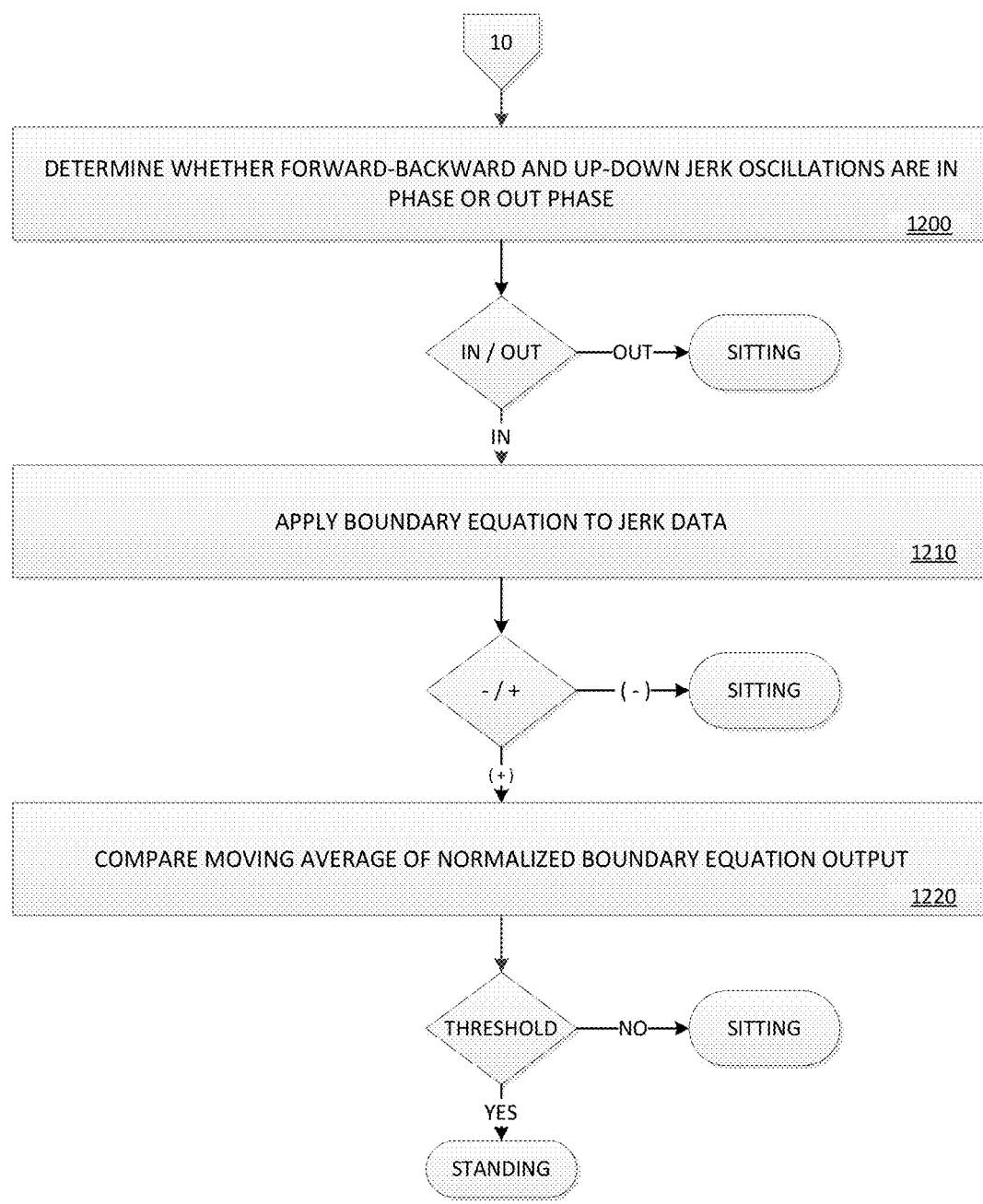

Aspects of the present disclosure further involve determining sitting versus standing cycling. The inventors have determined and discovered, through extensive testing, that a user's trunk accelerations are different when a cyclist is seated compared to when they are standing, and thus it is possible to determine the cyclist position (seated or standing) from the acceleration signals of a chest-worn device as described. Referring to FIGS. 10 and 12, in one specific implementation cyclist position may be determined by first obtaining raw acceleration values for each axis and feeding the values into a low pass filter (LPF) (operations 1000 and 1010). The LPF may have a corner/cut-off frequency of 1.5 Hz for the side-to-side axis, and 3 Hz for the up-down and forward-backward axes (the repetitive leg motions results in rhythmic trunk accelerations at double the cycling cadence frequency in the up-down and forward-backward direction, hence the doubled cut-off frequency). The derivative of each LPF output is then taken to calculate the jerk in three directions (jerk for each axes) (operation 1020). This effectively high pass filters the acceleration signals, removing the steady state offset. The jerk values for each axis are fed into an LPF. These LFP's might have corner/cutoff frequencies similar to the acceleration LPF's.

Referring now to FIG. 12, the system now determines whether the forward-backward and up-down jerk oscillations are in-phase or 180 degrees out of phase by comparing timing of zeros crossings between the two signals (operation 1200). If forward-backward and up-down jerk oscillations are in phase, the system proceeds to operation 1210. If, however, the oscillation are out of phase, the system determine that the cyclist is sitting. From extensive study, it is believed that that forward-backward and up-down accelerations are in-phase/180 degrees out of phase when a cyclist is standing in the large majority of the cases.

However, if the oscillations are in phase, it cannot similarly be assumed that the cyclist is standing. Instead, if forward-backward and up-down jerk oscillations are in phase, the system uses a boundary equation taking cadence and jerk ranges as inputs to determine instantaneous position (operation 1210). This boundary equation may have the following form:

Position=$b1$*cadence+$b2$*rangeXJerk+
    $b3$*rangeYJerk+$b4$*rangeZJerk+$b5$ $b1 \ldots b4$ and $b5$ are the linear coefficients and constant term of the boundary equation, respectively. These coefficient may be determined a priory using discriminant analysis and a set of training data (data for which cycling position is known). A calculated position of 0 might indicate sitting, whereas a calculated position of 1 might indicate standing.

Instantaneous position is fed into a moving average filter to reduce rapid fluctuations in position due to incorrectly detected position. If the output of the moving average filter is below some predefined threshold, for example 0.5, it may be assumed the cyclist is sitting (operation 1220). If the output of the moving average filter is above some predefined threshold, for example 0.5, it may be assumed the cyclist is standing (operation 1220). The threshold for standing and sitting detection might vary to introduce hysteresis.

Streaming to Device

The data collected by the device may be streamed or otherwise communicate to a computing device, such as a smart phone, tablet, personal computer, or the like, for display and recording.

Figure 13:
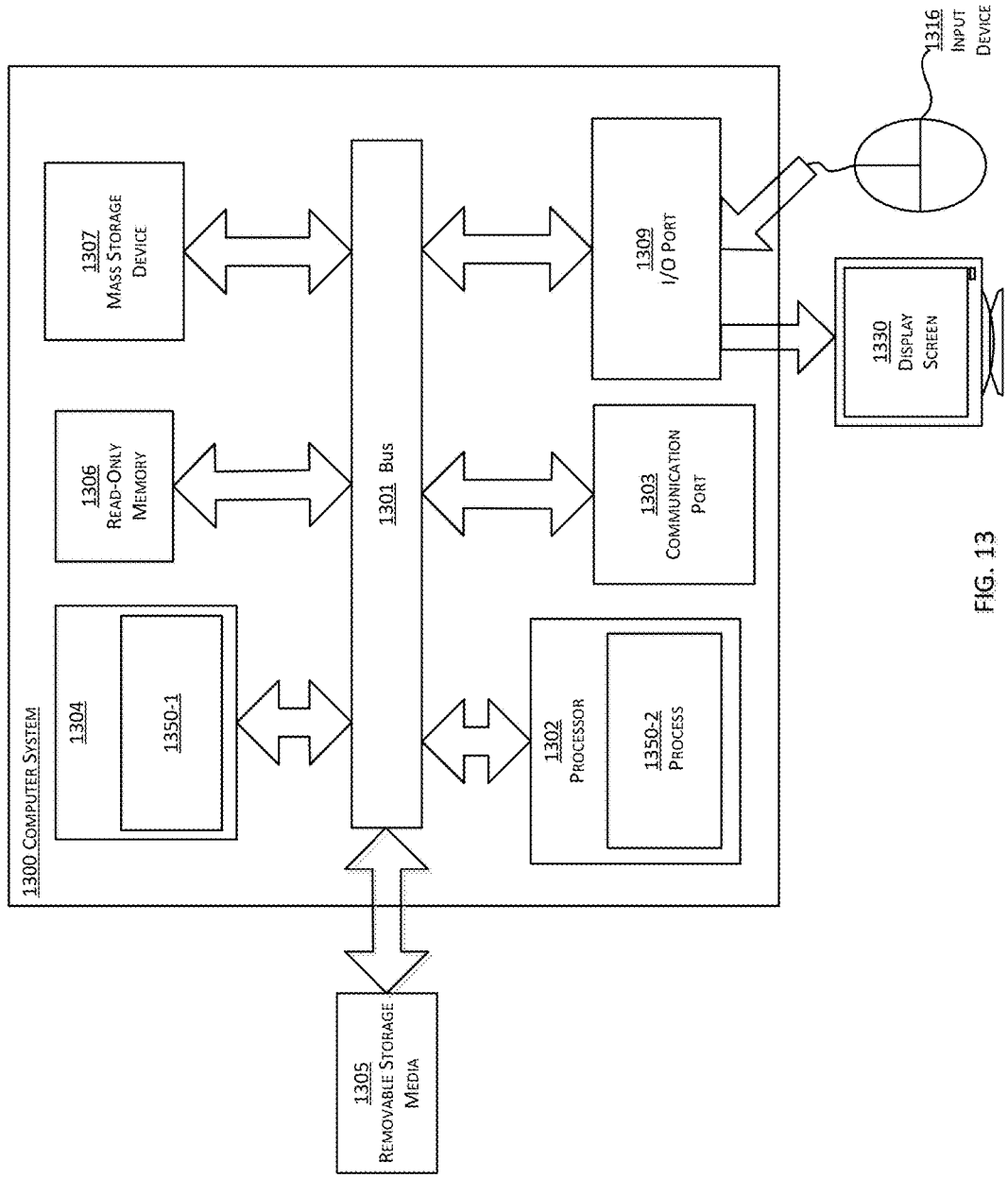
FIG. 13 is a general purpose computer that may implement aspects of the various methodologies and processes discussed herein.

Referring now to FIG. 13, aspects of the present disclosure may be conducted using a computing system 1300. The computer system may include one or more components connected via a bus 1301. In one implementation, the computer system includes at least one processor 1302 or other computing unit, which may include one or more internal levels of cache and a bus controller or bus interface unit to direct interaction with the bus. The processor may include a module 1350-1352 that specifically implements the various methods and systems discussed herein. Main memory 1304 may include one or more memory cards and a control circuit or other forms of removable memory 1305 and may store an application 1350-1351 including computer executable instructions, that when run on the processor, implement the methods, or portions thereof, and system set out herein. Other forms of memory, such as mass storage device, read only memory, and removable storage media, may also be included and accessible, by the processor via the bus.

The computer system may further include a communication port 1303 connected to a transport and/or transit network by way of which the computer system may receive network data useful in executing the methods and system set out herein as well as transmitting information and network configuration changes determined thereby. The computer system may include an I/O port 1309 connected to an I/O device, or other device, by which information is displayed, such as at display screen 1330, or information is input, such as input device 1316. The input device may be alphanumeric input device, including alphanumeric and other keys for communicating information and/or command selections to the processor. The input device may be another type of user input device including cursor control, such as a mouse, a trackball, or cursor direction keys for communicating direction information and command selections to the processor and for controlling cursor movement on the display device. In the case of a tablet or smart phone device, the input may be through a touch screen, voice commands, and/or Bluetooth connected keyboard, among other input mechanisms.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product that may include a machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

The description above includes example systems, methods, techniques, instruction sequences, and/or computer program products that embody techniques of the present disclosure. However, it is understood that the described disclosure may be practiced without these specific details. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

We claim:

1. A device comprising:
a housing coupled with a strap configured to secure the housing to a torso of a user;
an accelerometer in communication with a computing unit disposed in the housing, the accelerometer configured to communicate acceleration data associated with movements of the user to the computing unit;
the computing unit configured to:
obtain, from the accelerometer, a first plurality of acceleration values along a vertical axis and a second plurality of acceleration values along a second axis;
obtain, a first plurality of jerk values for the first plurality of acceleration values and a second plurality of jerk values for the second plurality of acceleration values;
detect a first series of zero crossings for the first plurality of jerk values and a second series of zero crossings for the second plurality of jerk values;

from the first series of zero crossing and the second series of zero crossing, compute at least one of riding cadence, a standing riding identifier or a sitting riding identifier.

2. The device of claim 1 further comprising:
a computing unit disposed within the housing and in communication with a pair of electrodes, the pair of electrodes configured to detect heart rate signals from the user, the computing unit coupled with a memory to store processed heart rate signals; and a wireless transmitter supported in the housing and operably coupled with the computing unit.

3. A device comprising:
a housing coupled with a strap configured to secure the housing to a torso of a user;
an accelerometer in communication with the computing unit disposed within the housing, the accelerometer configured to communicate acceleration data associated with movements of the user to the computing unit;
the computing unit configured to obtain cycle riding cadence through computer executable instructions for:
obtaining, from the accelerometer, a first plurality of acceleration values along a vertical axis and a second plurality of acceleration values along a second axis;
obtaining a first plurality of jerk values for the first plurality of acceleration values and a second plurality of jerk values for the second plurality of acceleration values;
detecting a first series of zero crossings for the first plurality of jerk values and a second series of zero crossings for the second plurality of jerk values;
obtaining a first set of time durations between the first series of zero crossings and a second set of time durations between the second series of zero crossings; and
identifying a riding cadence value based on whether the first set of time durations or the second set of time durations has a lower variability.

4. The device of claim 3 wherein the second axis is a side-to-side axis, and the riding cadence is based on the variability in the set of durations between vertical oscillation or side-to-side oscillation.

5. The device of claim 4, the computing unit further configured to:
filter the first plurality of acceleration values with a filter having a first cutoff frequency and the second plurality of acceleration values with a second filter having about double the first cutoff frequency of the first filter.

6. The device of claim 5 wherein the first cutoff frequency is 1.5 Hz and the second cutoff frequency is 3 Hz.

7. A device comprising:
a housing coupled with a strap configured to secure the housing to a torso of a user;
an accelerometer in communication with the computing unit disposed within the housing, the accelerometer configured to communicate acceleration data associated with movements of the user to the computing unit;
the computing unit including computer executable instructions to determine whether the user while cycling is standing or seated comprising:
obtaining, from the accelerometer, a first plurality of acceleration values along a vertical axis and a second plurality of acceleration values along a forward-backward axis;
obtaining a first plurality of jerk values for the first plurality of acceleration values and a second plurality of jerk values for the second plurality of acceleration values;
detecting a first series of zero crossings for the first plurality of jerk values and a second series of zero crossings for the second plurality of jerk values;
when the first series of zero crossing are out of phase with the second plurality of zero crossings, providing a seated riding identifier;
when the first series of zero crossing are in phase with the second plurality of zero crossings, applying a boundary equation to the first plurality of jerk values and the second plurality of jerk values and cadence, and
when a moving average of the normalized boundary equation output exceeds a threshold, providing a standing riding identifier.

8. A method comprising:
obtaining, at a computing unit, from an accelerometer, a first plurality of acceleration values along a vertical axis and a second plurality of acceleration values along a second axis;
obtaining, using the computing unit, a first plurality of jerk values for the first plurality of acceleration values and a second plurality of jerk values for the second plurality of acceleration values;
identifying, using the computing unit, a first series of zero crossings for the first plurality of jerk values and a second series of zero crossings for the second plurality of jerk values;
identifying, using the computing unit, a first set of time durations between the first series of zero crossings and a second set of time durations between the second series of zero crossings; and
identifying, using the computing unit, a riding cadence value based on whether the first set of time durations or the second set of time durations has a lower variability.

9. The method of claim 8 wherein the second axis is a side-to-side axis, and the riding cadence is based on the variability in the set of durations between vertical oscillation or side-to-side oscillation.

10. The method of claim 8 further comprising generating a signal to display the riding cadence value at a display.

11. The method of claim 8 wherein:
the computing unit is disposed within a housing supportable at the chest of a user; and
the accelerometer is in communication with the computing unit, the accelerometer configured to communicate acceleration data associated with movements of the user to the computing unit, the computing unit further configured to generate and store processed acceleration data in a memory coupled with the computing unit and within the housing.

12. The method of claim 8 wherein the computing unit is disposed within a housing supportable at a chest of a user, the computing unit in communication with a pair of electrodes, the pair of electrodes configured to detect heart rate signals from the user, the computing unit coupled with a memory to store processed heart rate signals.

13. The method of claim 8 wherein a memory is coupled with the computing unit, the memory including computer executable instructions to perform the method of claim 8.

14. A method comprising:
obtaining, at a computing unit, from an accelerometer, a first plurality of acceleration values along a vertical axis and a second plurality of acceleration values along a forward-backward axis;

obtaining, at the computing unit, a first plurality of jerk values for the first plurality of acceleration values and a second plurality of jerk values for the second plurality of acceleration values;

detecting, at the computing unit, a first series of zero crossings for the first plurality of jerk values and a second series of zero crossings for the second plurality of jerk values;

when the first series of zero crossing are in phase with the second plurality of zero crossings, providing, by the computing unit, a seated riding identifier;

when the first series of zero crossing are out of phase with the second plurality of zero crossings, applying a boundary equation to the first plurality of jerk values and the second plurality of jerk values and cadence;

when a moving average of the normalized boundary equation output exceeds a threshold, providing, by the computing unit, a standing riding identifier.

15. The method of claim 14 further comprising generating a signal to display the seated riding identifier or the standing riding identifier at a display.

16. The method of claim 14 wherein:

the computing unit is disposed within a housing configured to be supported on the chest of a user; and the accelerometer is in communication with the computing unit, the accelerometer configured to communicate acceleration data associated with movements of the user to the computing unit, the computing unit further configured to generate and store processed acceleration data in a memory coupled with the computing unit and within the housing.

17. The method of claim 14 wherein a memory is coupled with the computing unit, the memory including computer executable instructions to perform the method of claim 14.

18. The device of claim 3 wherein the computing unit disposed within the housing and in communication with a pair of electrodes, the pair of electrodes configured to detect heart rate signals from the user, the computing unit coupled with a memory to store processed heart rate signals, the computing unit further configured to generate and store processed acceleration data in the memory.

19. The device of claim 7 wherein the computing unit disposed within the housing and in communication with a pair of electrodes, the pair of electrodes configured to detect heart rate signals from the user, the computing unit coupled with a memory to store processed heart rate signals, the computing unit further configured to generate and store processed acceleration data in the memory.

* * * * *